United States Patent
Wachter et al.

(10) Patent No.: US 6,306,911 B1
(45) Date of Patent: Oct. 23, 2001

(54) SUBSTITUTED AMINO ACIDS AS NEUTRAL SPHINGOMYELINASE INHIBITORS

(75) Inventors: Michael P. Wachter, North Bloomsburg; Praful Lalan, Somerset, both of NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/499,426

(22) Filed: Feb. 7, 2000

(51) Int. Cl.[7] ............... A61K 31/195; A61K 31/381; A61K 31/4709; C07C 229/00; C07C 237/06; C07D 401/12

(52) U.S. Cl. ............... 514/567; 514/311; 514/314; 514/332; 514/337; 514/351; 514/443; 514/444; 514/438; 514/539; 514/561; 514/563; 514/569; 546/174; 546/264; 549/58; 549/59; 549/77; 560/38; 562/433; 562/439; 562/442; 562/443; 562/445; 562/451; 564/164

(58) Field of Search ............... 560/38; 562/433, 562/439, 442, 443; 549/58, 59, 77; 546/174, 264; 514/539, 567, 569, 443, 444, 438, 311, 314, 332, 337, 351, 561, 563

(56) References Cited

U.S. PATENT DOCUMENTS 6,107,520 * 8/2000 Rinehart ............... 564/360

FOREIGN PATENT DOCUMENTS

| 07-258132 | 10/1995 | (JP) . |
| 7-258132 * | 10/1995 | (JP) . |
| 8-53387 * | 2/1996 | (JP) . |
| 08-053387 | 2/1996 | (JP) . |
| 08-134002 | 5/1996 | (JP) . |
| 8-134002 * | 5/1996 | (JP) . |
| WO 99/54279 | 10/1999 | (WO) . |

OTHER PUBLICATIONS

Chatterjee, Subroto. Neutral sphingomyelinase: past, present and future. Chemistry And Physics of Lipids. 102, 79–96 (1999).

* cited by examiner

Primary Examiner—Evelyn Mei Huang
(74) Attorney, Agent, or Firm—John W. Wallen, III

(57) ABSTRACT

This invention relates to a series of substituted amino acids of Formula I

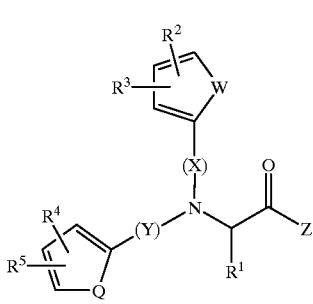

pharmaceutical compositions containing them and intermediates used in their manufacture. The compounds of the invention are small molecules that bind to neutral sphingomyelinase and inhibit its activity.

8 Claims, No Drawings

SUBSTITUTED AMINO ACIDS AS NEUTRAL SPHINGOMYELINASE INHIBITORS

BACKGROUND OF THE INVENTION

Neutral sphingomyelinase is a magnesium sensitive enzyme that is a member of the sphingomyelinase family, that catalyzes the hydrolytic cleavage of sphingomyelin to ceramide and phosphocholine at neutral pH optima. Ceramide and phosphocholine have a role as lipid second messengers in multiple signal transduction pathways including pathways involved in cell proliferation, apoptosis, and differentiation. Neutral sphingomyelinase may be involved in a wide variety of human diseases and conditions, including insulin resistant diabetes, arthritis, inflammation, cancer, and atherosclerosis. A review of the properties of Neutral sphingomyelinase is found in Chatterjee, S., Chemistry and Physics of Lipids, 102 (1999) pp79–96.

This invention relates to a series of small molecules that bind to neutral sphingomyelinase and inhibit the enzyme's activity. The invention includes pharmaceutical compositions containing these compounds, their methods of production as well as intermediates used in their synthesis. The present invention also includes methods of treating a patient suffering from a disorder that is related to the activity of neutral sphingomyelinase.

SUMMARY OF THE INVENTION

The disclosed invention contemplates a series of small molecules that demonstrate inhibition of neutral sphingomyelinase, an enzyme that cleaves sphingomyelin to yield ceramide and phosphocholine. As such these compounds are potentially useful in the treatment of diseases associated with neutral sphingomyelinase. In addition, the invention contemplates methods of producing these compounds and intermediates used in their manufacture.

The invention includes compounds of the Formula I:

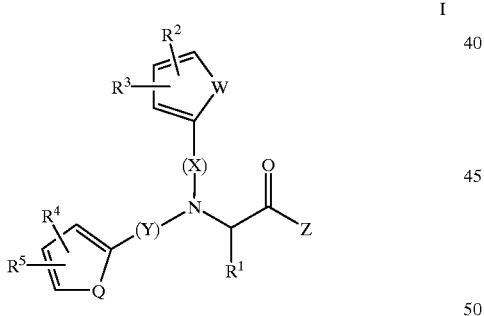

I wherein:
  $R^1$ is the side chain of a natural or unnatural-amino acids, where if said side chain contains a protectable group, that group may be protected with a member of the group consisting of succinyl, glutaryl, 3,3-dimethylglutaryl, $C_{1-5}$alkyl, $C_{1-5}$alkoxycarbonyl, acetyl, N-(9-fluorenylmethoxycarbonyl), trifluoroacetyl, omega-carboxy$C_{1-5}$alkylcarbonyl, t-butoxycarbonyl, benzyl, benzyloxycarbonyl, 2-chlorobenzyloxycarbonyl, phenylsulfonyl, ureido, t-butyl, cinnamoyl, trityl, 4-methyltrityl, 1-(4,4-dimethyl-2,6-dioxocyclohexylidene)ethyl, tosyl, 4-methoxy-2,3,6-trimethylbenzenesulfonyl, phenylureido, and substituted phenylureido (where the phenyl substituents are phenoxy, halo, $C_{1-5}$alkoxycarbonyl);

$R^2$ and $R^3$
  may be taken together to form a six-membered aromatic ring which is fused to the depicted ring, or are independently selected from the group consisting of hydrogen, $C_{1-5}$ alkyl, $C_{1-5}$ alkoxy, hydroxy, halo, trifluoromethyl, nitro, amino, phenyl, phenoxy, phenyl$C_{1-5}$alkyl, phenyl $C_{1-5}$alkoxy,
  substituted phenyl (where the substituents are selected from $C_{1-5}$alkyl, $C_{1-5}$ alkoxy, hydroxy, halo, trifluoromethyl, nitro, nitrile, and amino),
  substituted phenoxy (where the substituents are selected from $C_{1-5}$ alkyl, $C_{1-5}$ alkoxy, hydroxy, halo, trifluoromethyl, nitro, nitrile, and amino),
  substituted phenyl$C_{1-5}$alkyl (where the substituents are selected from $C_{1-5}$ alkyl, $C_{1-5}$ alkoxy, hydroxy, halo, trifluoromethyl, nitro, nitrile, and amino),
  substituted phenyl$C_{1-5}$alkoxy (where the substituents are selected from $C_{1-5}$ alkyl, $C_{1-5}$ alkoxy, hydroxy, halo, trifluoromethyl, nitro, nitrile, and amino), and
  substituted amino (where the substituents are selected from one or more members of the group consisting of $C_{1-5}$alkyl, halosubstituted$C_{1-5}$alkyl, $C_{1-5}$alknyl, $C_{1-5}$alkenyl, phenyl, phenyl$C_{1-5}$alkyl, $C_{1-5}$alkylcarbonyl, halo substituted $C_{1-5}$alkylcarbonyl, carboxy$C_{1-5}$alkyl, $C_{1-5}$alkoxy$C_{1-5}$alkyl, cinnamoyl, naphthylcarbonyl, furylcarbonyl, pyridylcarbonyl, $C_{1-5}$alkylsulfonyl, phenylcarbonyl, phenyl$C_{1-5}$alkylcarbonyl, phenylsulfonyl, phenyl$C_{1-5}$alkylsulfonyl substituted phenylcarbonyl, substituted phenyl$C_{1-5}$alkylcarbonyl, substituted phenylsulfonyl, substituted phenyl$C_{1-5}$alkylsulfonyl, substituted phenyl, and substituted phenyl$C_{1-5}$alkyl [where the aromatic phenyl, phenyl$C_{1-5}$alkyl, phenylcarbonyl, phenyl$C_{1-5}$alkylcarbonyl, phenylsulfonyl, and phenyl$C_{1-5}$alkylsulfonyl substitutents are independently selected from one to five members of the group consisting of $C_{1-5}$alkyl, $C_{1-5}$alkoxy, hydroxy, halogen, trifluoromethyl, nitro, nitrile, and amino]);

$R^4$ and $R^5$
  may be taken together to form a six-membered aromatic ring which is fused to the depicted ring, or are independently selected from the group consisting of hydrogen, $C_{1-5}$ alkyl, $C_{1-5}$ alkoxy, hydroxy, halo, trifluoromethyl, nitro, amino, phenyl, phenoxy, phenyl$C_{1-5}$alkyl, phenyl $C_{1-5}$alkoxy,
  substituted phenyl (where the substituents are selected from $C_{1-5}$alkyl, $C_{1-5}$ alkoxy, hydroxy, halo, trifluoromethyl, nitro, nitrile, and amino),
  substituted phenoxy (where the substituents are selected from $C_{1-5}$ alkyl, $C_{1-5}$ alkoxy, hydroxy, halo, trifluoromethyl, nitro, nitrile, and amino),
  substituted phenyl$C_{1-5}$alkyl (where the substituents are selected from $C_{1-5}$ alkyl, $C_{1-5}$ alkoxy, hydroxy, halo, trifluoromethyl, nitro, nitrile, and amino),
  substituted phenyl$C_{1-5}$alkoxy (where the substituents are selected from $C_{1-5}$ alkyl, $C_{1-5}$ alkoxy, hydroxy, halo, trifluoromethyl, nitro, nitrile, and amino), and
  substituted amino (where the substituents are selected from one or more members of the group consisting of $C_{1-5}$alkyl, halosubstituted$C_{1-5}$alkyl, $C_{1-5}$alknyl, $C_{1-5}$alkenyl, phenyl, phenyl$C_{1-5}$alkyl, $C_{1-5}$alkylcarbonyl, halo substituted $C_{1-5}$alkylcarbonyl, carboxy$C_{1-5}$alkyl, $C_{1-5}$alkoxy$C_{1-5}$alkyl, cinnamoyl, naphthylcarbonyl, furylcarbonyl, pyridylcarbonyl, $C_{1-5}$alkylsulfonyl, phenylcarbonyl, phenyl$C_{1-5}$alkylcarbonyl, phenylsulfonyl, phenyl$C_{1-}$ ₅alkylsulfonyl substituted phenylcarbonyl, substituted phenylC$_{1-5}$alkylcarbonyl, substituted phenylsulfonyl, substituted phenylC$_{1-5}$alkylsulfonyl, substituted phenyl, and substituted phenylC$_{1-5}$alkyl [where the aromatic phenyl, phenylC$_{1-5}$alkyl, phenylcarbonyl, phenylC$_{1-5}$alkylcarbonyl, phenylsulfonyl, and phenylC$_{1-5}$alkylsulfonyl substitutents are independently selected from one to five members of the group consisting of C$_{1-5}$alkyl, C$_{1-5}$alkoxy, hydroxy, halogen, trifluoromethyl, nitro, nitrile, and amino]);

W is selected from the group consisting of —CH=CH—, —S—, and —CH=N—;

Q is selected from the group consisting of —CH=CH—, —S—, and —CH=N—;

X is selected from the group consisting of carbonyl, C$_{1-5}$alkyl, C$_{1-5}$alkenyl, C$_{1-5}$alkenylcarbonyl, C$_{2-5}$alkynyl, C$_{2-5}$alkynylcarbonyl and (CH$_2$)$_m$—C(O)— where m is 2–5;

Y is selected from the group consisting of carbonyl, C$_{1-5}$alkyl, C$_{1-5}$alkenyl, C$_{1-5}$alkenylcarbonyl, C$_{2-5}$alkynyl, C$_{2-5}$alkynylcarbonyl and (CH$_2$)$_m$—C(O)— where m is 2–5;

Z is selected from the group consisting of hydroxy, C$_{1-5}$ alkoxy, phenoxy, phenylC$_{1-5}$alkoxy, amino, C$_{1-5}$alkylamino, diC$_{1-5}$alkylamino, phenylamino, phenylC$_{1-5}$alkylamino, piperidin-1-yl
 substituted piperidin-1-yl (where the substituents are selected from the group consisting of C$_{1-5}$alkyl, C$_{1-5}$alkoxy, halo, aminocarbonyl, C$_{1-5}$alkoxycarbonyl, and oxo;
 substituted phenylC$_{1-5}$alkylamino (where the aromatic substitutents are selected from the group consisting of C$_{1-5}$alkyl, C$_{1-5}$alkoxy, phenylC$_{1-5}$alkenyloxy, hydroxy, halogen, trifluoromethyl, nitro, nitrile, and amino),
 substituted phenoxy (where the aromatic substitutents are selected from the group consisting of C$_{1-5}$alkyl, C$_{1-5}$alkoxy, hydroxy, halogen, trifluoromethyl, nitro, nitrile, and amino),
 substituted phenylC$_{1-5}$alkoxy (where the aromatic substitutents are selected from the group consisting of C$_{1-5}$alkyl, C$_{1-5}$alkoxy, hydroxy, halogen, trifluoromethyl, nitro, nitrile, and amino),
 —OCH$_2$CH$_2$(OCH$_2$CH$_2$)$_s$OCH$_2$CH$_2$O—, —NHCH$_2$CH$_2$(OCH$_2$CH$_2$)$_s$OCH$_2$CH$_2$NH—, —NH(CH$_2$)$_p$O(CH$_2$)$_q$O(CH$_2$)$_p$NH—, —NH(CH$_2$)$_q$NCH$_3$(CH$_2$)$_s$NH—, —NH(CH$_2$)$_s$NH—, and (NH(CH$_2$)$_s$)$_3$N,
 where s, p, and q are independently selected from 1–7 and the salts thereof.

DETAILED DESCRIPTION OF THE INVENTION

The terms used in describing the invention are commonly used and known to those skilled in the art. "Independently" means that when there are more than one substituent, the substituents may be different. The term "alkyl" refers to straight, cyclic and branched-chain alkyl groups and "alkoxy" refers O-alkyl where alkyl is as defined supra. "Cbz" refers to benzyloxycarbonyl. "Boc" refers to t-butoxycarbonyl and "Ts" refers to toluenesulfonyl. "DCC" refers to 1,3-dicyclohexylcarbodiimide, "DMAP" refers to 4-N',N-dimethylaminopyridine and "HOBT" refers to 1-hydroxybenzotriazole hydrate. "Fmoc" refers to N-(9-fluorenylmethoxycarbonyl), "DABCO" refers to 1,4-Diazabicyclo[2.2.2]octane, "EDCI" refers to 1-(3-dimethylaminopropyl)-3-ethylcarbodiimide, and "Dde" refers to 1-(4,4-dimethyl-2,6-dioxocyclohexylidene)ethyl. The side chains of α-amino acids refer to the substituents of the stereogenic carbon of an α-amino acid. For example if the amino acid is lysine, the side chain is 1-aminobutan-4-yl. The term natural amino acid refers to the 20 α-amino acids of the L configuration which are found in natural proteins. Unnatural α-amino acids include synthetic amino acids such as -aminoadipic acid, 4-aminobutanoic acid, 6-aminohexanoic acid, aminosuberic acid, 5-aminopentanoic acid, p-aminophenylalanine, -aminopimelic acid -carboxyglutamic acid, p-carboxyphenylalanine, carnitine, citrulline, -diaminopropionic acid, -diaminobutyric acid, homocitrulline, homoserine, and statine as well as D-configuration amino acids. The term "protectable group" refers to a hydroxy, amino, carboxy, carboxamide, guanidine, amidine or a thiol groups on an amino acid side. Compounds of the invention may be prepared by following general procedures known to those skilled in the art, and those set forth herein.

The compounds of the invention may be prepared by liquid phase organic synthesis techniques or by using amino acids which are bound to a number of known resins. The underlying chemistry, namely, acylation and alkylation reactions, peptide protection and deprotection reactions as well as peptide coupling reactions use similar conditions and reagents. The main distinction between the two methods is in the starting materials. While the starting materials for the liquid phase syntheses are the N-protected amino acids or the lower alkyl ester derivatives of the N-protected amino acids, the starting material for the resin syntheses are amino acids which are bound to resins by their carboxy termini.

General Procedure For The Solid-Phase Synthesis
Of Symmetrical N,N-Disubstituted Amino Acids
Scheme 1.

An equivalent of an N-Fmoc-protected amino acid which is bound to a resin 1a is suspended in a suitable solvent such as DMF. This solvent is removed and the nitrogen protecting group (Fmoc) is removed by stirring the resin bound amino acid with an organic base, such as piperidine, and an addition portion of the solvent. A solution of about two to three equivalents of an appropriately substituted halide, 1b, and a suitable base such DIEA is added to the resin bound amino acid and this mixture is shaken for 18–36 h. The resulting mixture is washed with several portions of a suitable solvent and is suspended and shaken in an acidic solution, such as 50% TFA/CH$_2$Cl$_2$, over several hours to cleave the acid from the resin and give the N-disubstituted amino acid 1c.

By varying the resin bound amino acid 1a, one may obtain many of the compounds of the invention. The following resin bound amino acids may be used in Scheme I: alanine, N-g-(4-methoxy-2,3,6-trimethylbenzenesulfonyl)arginine, -(4-methyltrityl)asparagine, aspartic acid (-t-butyl ester), S-(trityl)cysteine, -(4-methyltrityl)glutamine, glutamic acid (-t-butyl ester), glycine, N-imidazolyl(trityl)histidine, isoleucine, leucine, N-(2-chlorobenzyloxycarbonyl)lysine, N-(t-butoxycarbonyl)lysine, methionine, phenylalanine, proline, O-(t-butyl)serine, O-(t-butyl)threonine, N-indolyl-(t-butoxycarbonyl)tryptophan, O-(t-butyl)tyrosine, valine, -alanine, -aminoadipic acid, 4-aminobutanoic acid, 6-aminohexanoic acid, -aminosuberic acid, 5-aminopentanoic acid, p-aminophenylalanine, -aminopimelic acid -carboxyglutamic acid, p-carboxyphenylalanine, carnitine, citrulline, -diaminopropionic acid, -diaminobutyric acid, homocitrullin, homoserine, and statine. In addition, the choice of "W" and "X" can be varied by using known halide derivatives of 1b. For example using benzylchloride, 2-chloromethylthiophene, or 2-chloromethylpyridine gives compounds of the invention where "W" is —CH=CH—, —S—, or —CH=N—, respectively. For variations in "X", the use of 2-chloroethylphenyl, 3-chloro-1-propenylbenzene, or benzeneacetyl chloride as 1b, give compounds where Y is $(CH_2)_2$, —CH=CH—CH$_2$—, or —CH$_2$C(O)— respectively. Still further, Scheme 1 may be used to produce combinatorial mixtures of products. Using mixtures of resin bound amino acids, 1a, with only one 1b produces said combinatorial mixtures. Alternatively, using one amino acid 1a with a mixture of 1b as well as mixture of 1a with mixtures of 1b gives a large range of combinatorial mixtures.

Scheme 1

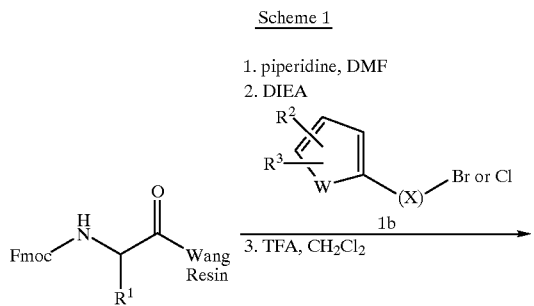

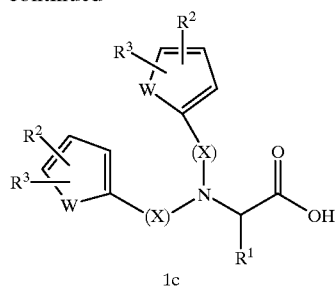

General Procedure for the Solid-Phase Synthesis of Unsymmetrical N,N-Disubstituted Amino Acids Scheme 2, Step A An equivalent of an N-Fmoc-protected amino acid which is bound to a resin 1a is suspended in a suitable solvent such as DMF. This solvent is removed and the nitrogen protecting group (Fmoc) is removed by stirring the resin bound amino acid with an organic base, such as piperidine, and an addition portion of the solvent. Trimethyl orthoformate and an appropriately substituted aldehyde 2a (5 equivalents) is added and the mixture is shaken under $N_2$ overnight. This mixture is treated with a suspension of NaBH(OAc)$_3$ (5 equivalents) in CH$_2$Cl$_2$ and shaken under $N_2$ overnight. After filtration and washing with a suitable solvent, the resulting product, resin bound N-monosubstituted amino acid 2b, is rinsed with a suitable solvent and its identity is confirmed by MS and or HPLC analysis after treatment of a portion of the resin with 50% TFA/CH$_2$Cl$_2$.

Scheme 2, Step B

The resin 2b is suspended in an appropriate solvent such as DMF and is filtered. The appropriately substituted alkyl or arylkyl halide, 2c, and an appropriate base such as DIEA are added with some additional solvent and the mixture is shaken under $N_2$ for 18–36 h. The resin bound N,N-disubstituted amino acid, 2d, is isolated from the suspension and the resin is cleaved with an acidic solution to give the free acid 2e.

Scheme 2

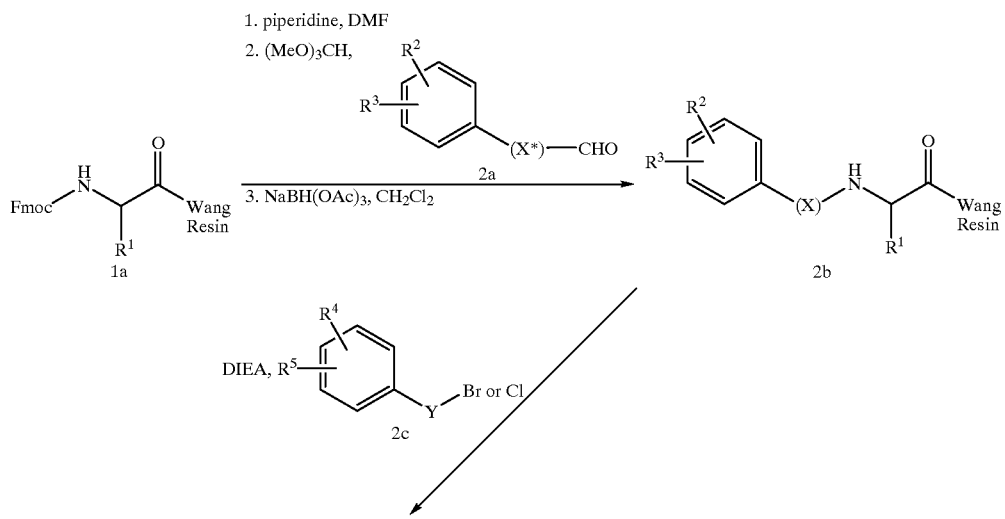

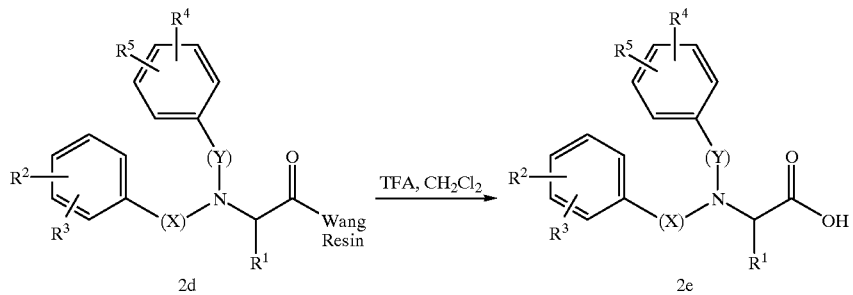

Scheme 3, Step C

A resin bound amine, 2d, where $R^4$ is nitro, is suspended in a suitable solvent, such as DMF, and is filtered. This mixture is treated with $SnCl_2$ dihydrate in DMF and shaken under $N_2$ overnight. The solvent is removed and the resin is washed successive portions of a suitable solvent to give the resin bound compound 3a where $R^4$ is amino. The resin is suspended in a suitable solvent and is combined with an organic base, such as pyridine an appropriately substituted carboxylic acid anhydride, acid chloride, or sulfonyl chloride. The mixture is shaken under $N_2$ overnight and is filtered to give the resin bound amino acid 3b. This material is treated with an acid and a suitable solvent to give the free amino acid 3b.

Scheme 3, Step D

The resin bound amine 3a is treated with TMOF and an appropriately substituted aldehyde 3c is added and the mixture is shaken under $N_2$ overnight. The resulting mixture is drained and treated with a suspension of $NaBH(OAc)_3$ in an appropriate solvent and this mixture is shaken under $N_2$ overnight. The resin bound 3-aralkylaminophenyl amino acid is identified my spectral techniques after cleavage to give the free acid 3d as previously described.

Scheme 3, Step E

Resin bound, 2d, where $R^1$ is $(CH_2)_4NH(Dde)$ is mixed with a suitable solvent, such as DMF, and shaken with successive portions of 2% solution of hydrazine hydrate in DMF over about 30 min. The resin is filtered and treated with a suitable solvent and a cyclic anhydride derivative 3e, and a base such as DMAP and pyridine. This mixture is shaken under $N_2$ overnight and filtered to give the resin bound amine, 3f. This material is identified by spectral techniques after cleavage to give the free acid 3f as previously described.

Scheme 3

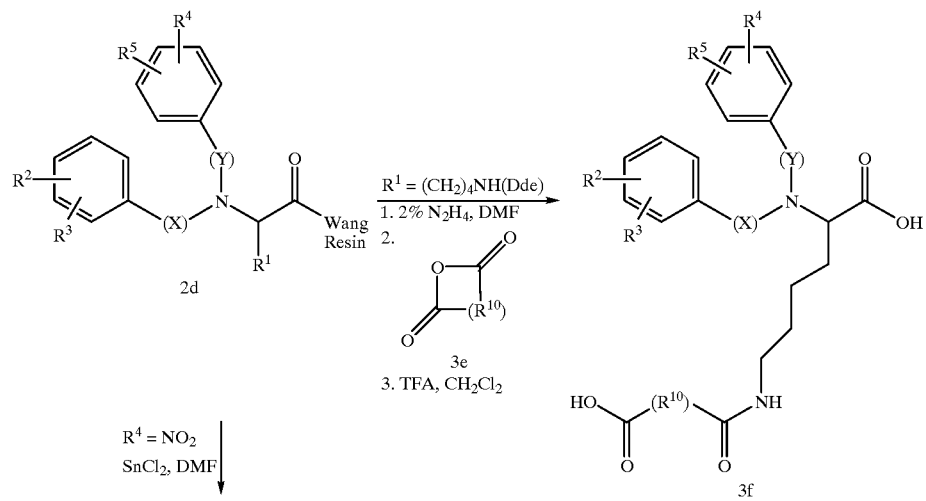

-continued

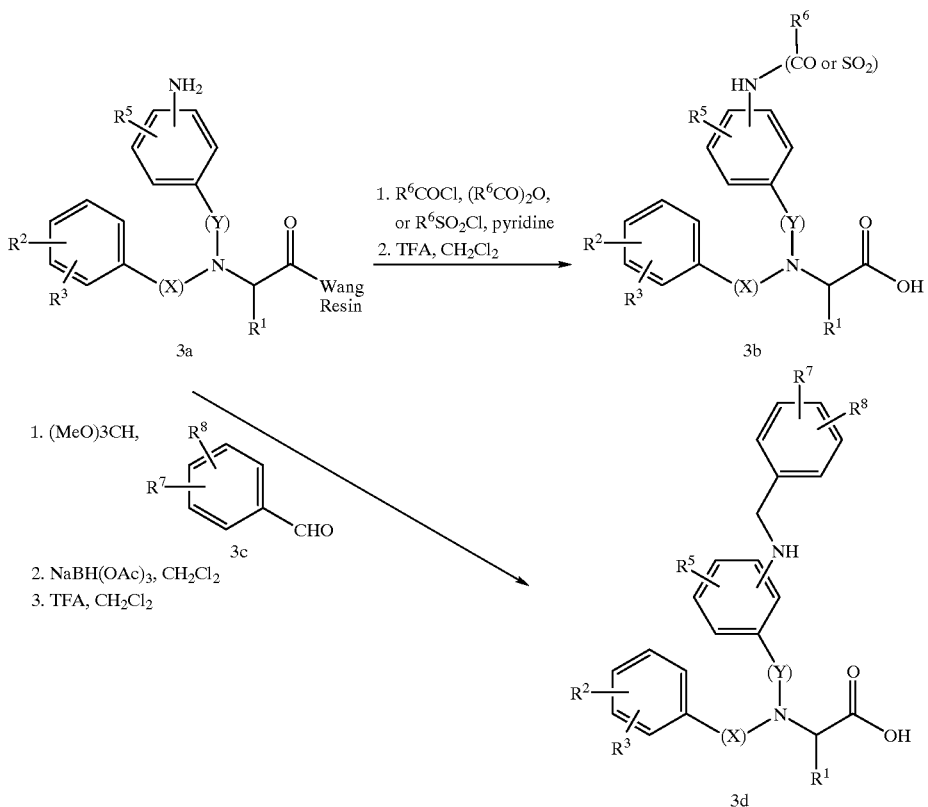

Scheme 4. Step F

Resin bound 2b, where $R^2$ is nitro is suspended in $CH_2Cl_2$ and is treated with an organic base, such as pyridine, and 9-fluorenylmethoxy chloride. This mixture is shaken under $N_2$ overnight, filtered and resuspended in a suitable solvent. This mixture is treated with $SnCl_2$ dihydrate in DMF and shaken under $N_2$ overnight. The solvent is removed and the resin is washed successive portions of a suitable solvent and filtered to give the resin bound compound 4a where $R^2$ is amino. The resin 4a is then suspended in a suitable solvent, such as $CH_2Cl_2$, and is combined with 0.4 mmol of pyridine and 0.25–0.4 mmol of the appropriately substituted carboxylic acid anhydride, acid chloride, or sulfonyl chloride. The mixture is shaken under $N_2$ overnight, filtered, and washed successively with three portions each of $CH_2Cl_2$ and MeOH. This resin is suspended in DMF, filtered, and shaken under $N_2$ with 5 mL of a 40% solution of piperidine in DMF. After 1 h, the solvent is drained and the resin was washed successively with three portions each of suitable solvents to give the resin bound 4b. The identity of the compound was confirmed by spectral analysis after cleavage as previously described.

Scheme 4

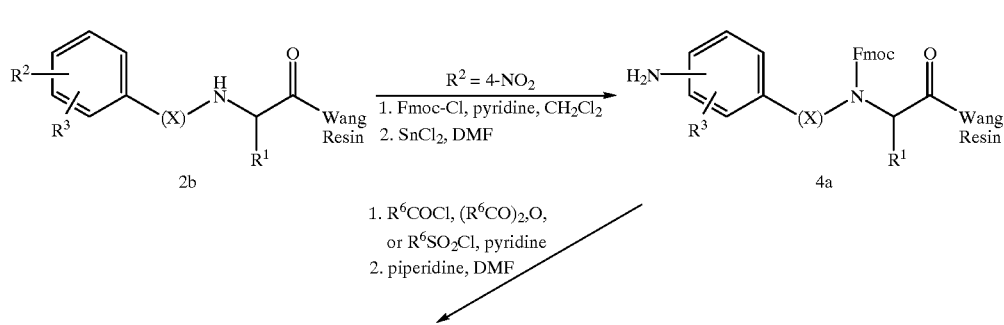

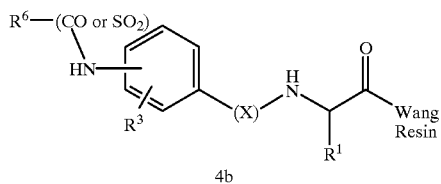

4b

Scheme 5

The resin 2b (0.2 mmol) is suspended in $CH_2Cl_2$, filtered, and is resuspended in $CH_2Cl_2$. This suspension is treated with diethyl phosphonoacetic acid and diisopropylcarbodiimide or other suitable carbodiimide reagent, and the mixture is shaken under $N_2$ overnight. The solvent is drained and the resulting resin 5a was washed successively with three portions each of $CH_2Cl_2$ and MeOH. The resin is suspended in DMF and filtered. A solution of the appropriately substituted aldehyde 5b (0.6–1.0 mmol) in 3–5 mL of DMF, lithium bromide (0.6–1.0 mmol), and a suitable base such as DIEA or $Et_3N$ (0.6–1.0 mmol) is added and the mixture is shaken under $N_2$ overnight. The solvent is removed and the resin is washed successively with three portions each of DMF, $CH_2Cl_2$, and MeOH. The identity of the resin bound substituted amino acid 5c was confirmed spectral techniques. The resin bound material may be treated with 50% $TFA/CH_2Cl_2$ over 1–1.5 h, to give the acid 5c.

base such as DIEA at room temperature over 16 h gives the dimer 6b.

Scheme 6

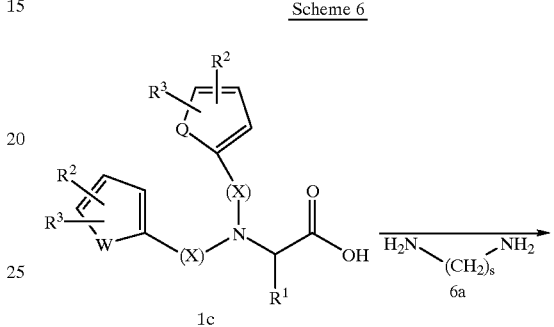

Scheme 5

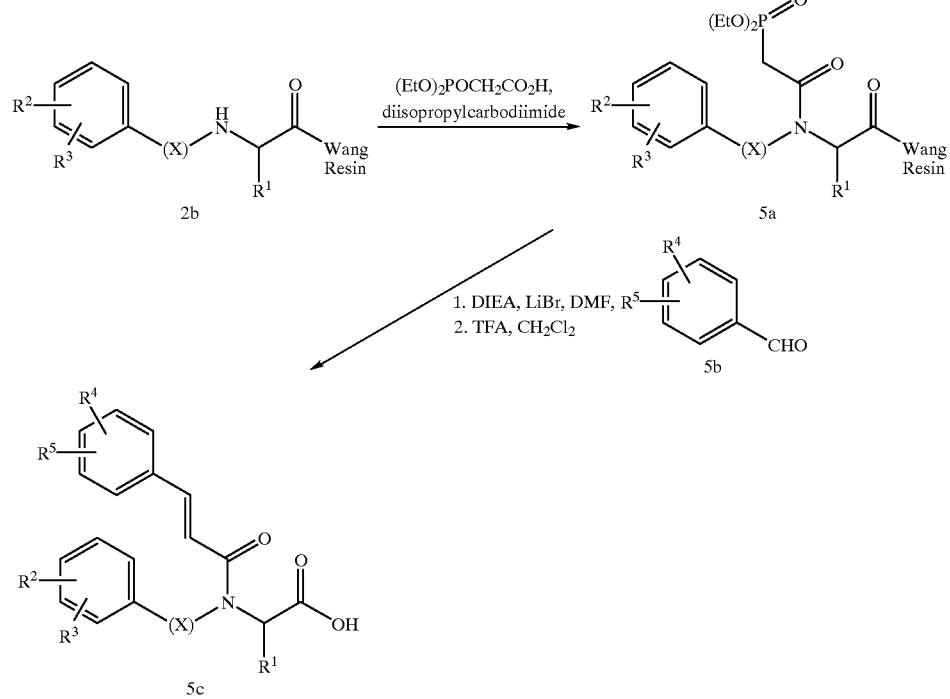

Scheme 6

To prepare dimer compounds where Z is $NH(CH_2)_sNH$, products of Schemes 1–5 may be used in Scheme 6. Treatment of two equivalents of the substituted amino acid 1c with an equivalent of the diamine 6a, in the presence of HOBT and a peptide coupling agent such as EDCI and a -continued

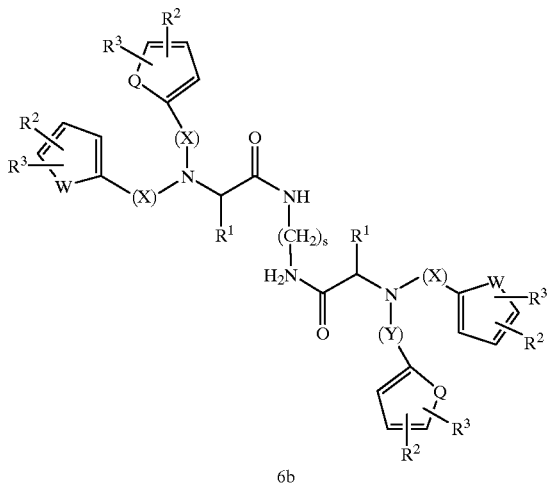

6b

General Procedure For The Solution-Phase Synthesis Of Symmetrical N,N-Disubstituted Amino Acids Scheme 7. Step A A solution of of amino acid ester 7a, an appropriately substituted halide derivative 1b, and an appropriate base such as DIFA, $Na_2CO_3$, or $Cs_2CO_3$ in a suitable solvent, such as DMF, is heated at 50–100° C. under $N_2$ overnight, or until the starting material is exhausted, to give a mixture of the di and mono-substituted amines. 7b and 7c respectively. If the side chains of $R^1$ contain acid cleavable protecting groups, those groups may be cleaved by treatment with 30–80% $TFA/CH_2Cl_2$. Esters 7b and 7c may be independently converted to the corresponding acids 7d and 7e by hydrolysis with an appropriate base such as aqueous NaOH.

An alternative method to generate a substituted bromide derivative can be achieved by stirring an alcohol derivative with with a 1M solution of $PBr_3$ in $CH_2Cl_2$ at room temperature for about 16 hrs. The reaction solution is extracted into EtOAc and washed with saturated NaCl solution. The organic phase is dried and concentrated to yield the product.

Scheme 7

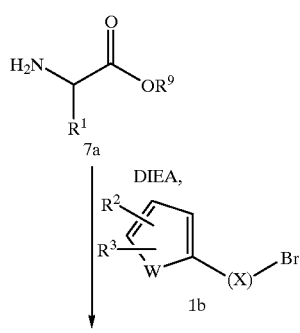

-continued

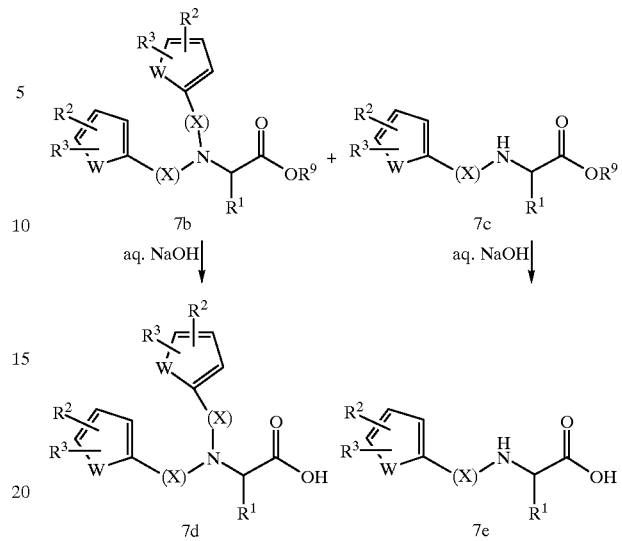

General Procedure For The Solution-Phase Synthesis Of Unsymmetrical N,N-Disubstituted Amino Acids Scheme 8, Step A A solution of 1 mmol of amino acid ester 8a (or the corresponding HCl salt and 1.1 mmol of DIEA) and 1–1.5 mmol of the appropriately substituted aldehyde 2a in 3–5 ml, of trimethyl orthoformate was stirred at room temperature under $N_2$ overnight. The solution was either concentrated and used directly for the next reaction, or was partitioned between EtOAc and water, washed with brine, dried over $Na_2SO_4$, and concentrated to give crude product, which was purified by MPLC to give mono-substituted product 8b.

Scheme 8, Step B

Amino ester 8b was dissolved in DMF, combined with 1.1–1.5 mmol of the appropriately substituted chloride or bromide 2c, and heated at 50–100° C. overnight. The reaction mixture was cooled and partitioned between water and EtOAc. The organic layer was washed three times with water and once with brine, dried over $Na_2SO_4$, and concentrated. The crude product was purified by MPLC to give pure 8c. For examples of 8c wherein the side chain $R^1$ contained an acid-cleavable protecting group such as t-butylcarbamate. t-butyl ester, or t-butyl ether, 8c was stirred in 30–80% $TFA/CH_2Cl_2$) for 1–3 h. The reaction mixture was concentrated and optionally dissolved in HOAc and freeze-dried to give the deprotected form of 8c. For examples of 8c where $R^9$ was equal to t-butyl, 8c was stirred in 30–80% TFA/$CH_2Cl_2$ for 1–3 h and treated as described above to give acid 8d. For examples of 8c where $R^9$ was equal to methyl, ethyl, or other primary or secondary alkyl esters, 8c was stirred with with 1–2 mmol of aqueous LiOH, NaOH, or KOH in MeOH, EtOH, or THF at 20–80° C. until TLC indicated the absence of 8c. The solution was acidified to pH 4–5 with aqueous citric acid or HCl and was extracted with $CH_2Cl_2$ or EtOAc. The organic solution was washed with brine, dried over $Na_2SO_4$, and concentrated to give 8d.

Scheme 8, Step C

For examples of amino acid ester 8c where $R^1(CH_2)_4NHBoc$, 8c (1 mmol) was stirred in 30–80% $TFA/CH_2Cl_2$ for 1–3 h. The reaction mixture was concentrated to provide 8e as the TFA salt. Optionally, the TFA salt was dissolved in $CH_2Cl_2$ or EtOAc and washed with aqueous NaOH or $Na_2CO_3$, dried over $Na_2SO_4$, and concentrated to give 8e as the free base.

Scheme 8, Step D

A solution of 1 mmol of 8e, 1–4 mmol of an appropriate base such as DIEA, and 1–2 mmol of the appropriately substituted cyclic anhydride 3e was stirred in $CH_2Cl_2$ or DMF under $N_2$ overnight. The resulting mixture was diluted with $CH_2Cl_2$ or EtOAc and washed with aqueous HCl, water, and brine, was dried over $Na_2SO_4$, and concentrated to provide 8f. Alternatively, 1 mmol of 8e 1–4 mmol of an appropriate base such as DIEA, and 1–2 mmol of the appropriately substituted carboxylic acid anhydride $(R^{11}CO)_2O$ or acid chloride $R^{11}COCl$ was stirred in $CH_2Cl_2$ or DMF under $N_2$ overnight and worked up as above to provide 8g. Alternatively, 1 mmol of 8e, 1–4 mmol of an appropriate base such as DIEA, and 1–2 mmol of the appropriately substituted isocyanate $R^{12}NCO$ was stirred in $CH_2Cl_2$ or DMF under $N_2$ overnight and worked up as above to provide 8h.

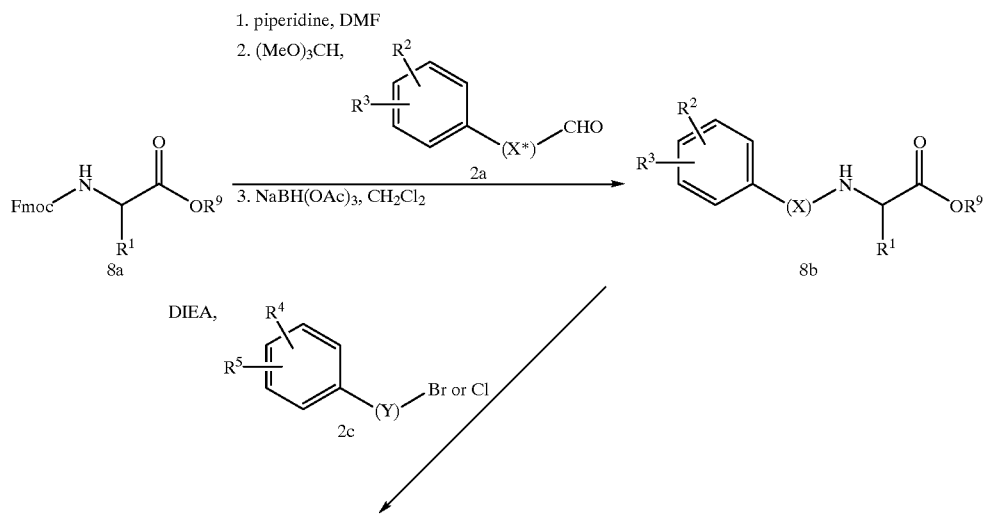

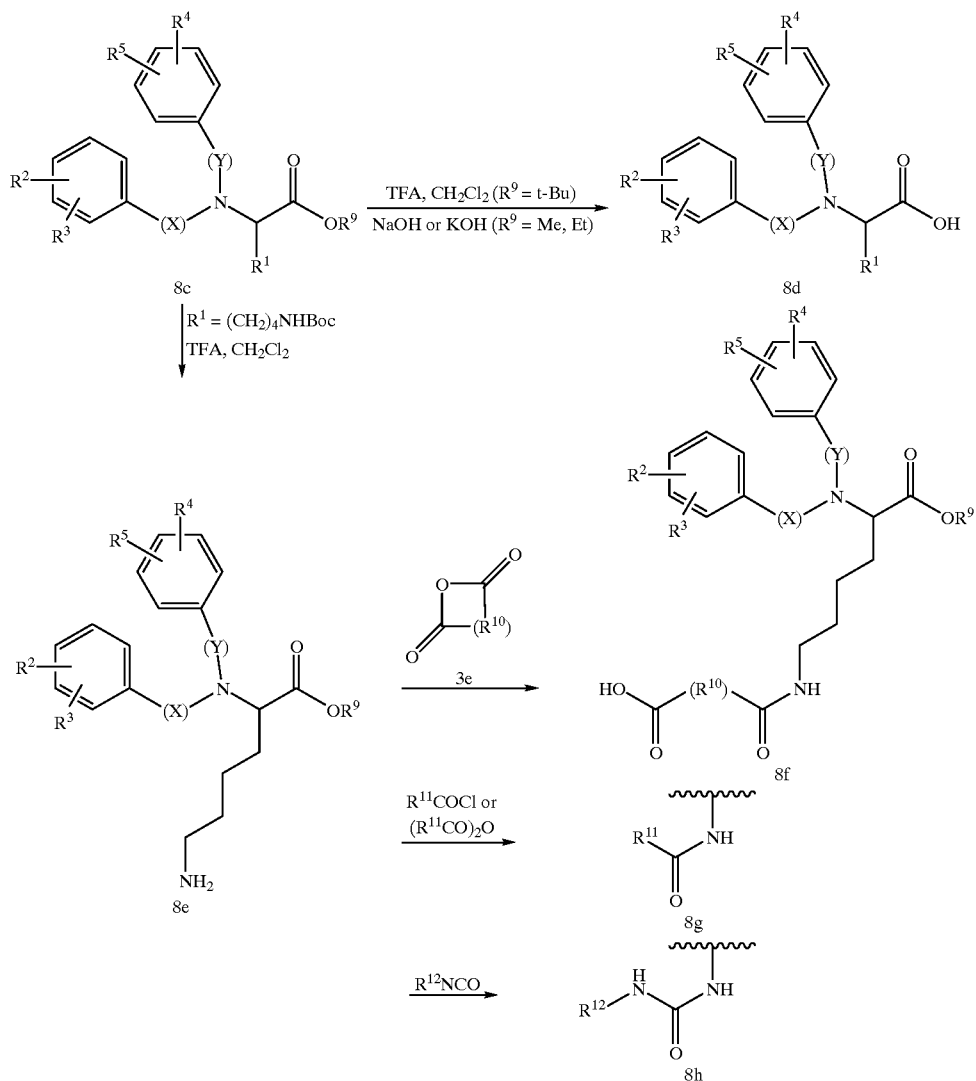

Scheme 9, Step A

For examples of 8c where $R^5$=$NO_2$, a solution of 1 mmol of 8c (where $R^2$, $R^3$, $R^4$, or) and 10–12 mmol of $SnCl_2$ dihydrate was stirred in MeOH, EtOH, or DMF at 20–80° C. for 0.5–24 h under $N_2$. The solution was taken to room temperature and poured into aqueous $Na_2CO_3$ with rapid stirring. The resulting mixture was extracted with EtOAc or $CH_2Cl_2$ and the organic extracts were washed with brine, dried over $Na_2SO_4$, and concentrated to give the aminophenyl product 9a, which was purified by MPLC or used without further purification.

Scheme 9, Step B

A solution of 1 mmol of aminophenyl compound 9a and 1–1.5 mmol of the appropriately substituted aldehyde 2a in 3–5 mL of trimethyl orthoformate was stirred at room temperature under $N_2$ overnight. The solution was either concentrated and used directly for the next reaction, or was partitioned between EtOAc and water, washed with brine, dried over $Na_2SO_4$, and concentrated to give crude product, which was purified by MPLC to give 9b. For examples of 9b wherein the side chain $R^1$ or $R^9$ contained an acid-cleavable protecting group such as t-butylcarbamate, t-butyl ester, or t-butyl ether, 9b was stirred in 30–80% TFA/$CH_2Cl_2$ for 1–3 h. The reaction mixture was concentrated and optionally dissolved in HOAc and freeze-dried to give the deprotected form of 9b.

Scheme 9, Step C

A solution of 1 mmol of 3-aminophenyl compound 9a, 1.1–2 mmol of pyridine, and 1–1.5 mmol of the appropriately substituted acid chloride, acid anhydride, or sulfonyl chloride in 3–5 mL of $CH_2Cl_2$ or $ClCH_2CH_2Cl$ was stirred at room temperature under $N_2$ overnight. The solution was partitioned between EtOAc and water, washed with water, saturated aqueous $NaHCO_3$, and brine, dried over $Na_2SO_4$, and concentrated to give crude product which was optionally purified by MPLC to give amide or sulfonamide 9c. For examples of 9c wherein the side chain $R^1$ or $R^9$ contained an acid-cleavable protecting group such as t-butylcarbamate t-butyl ester, or t-butyl ether, 9c was stirred in 30–80% TFA/$CH_2Cl_2$ for 1–3 h. The reaction mixture was concentrated and optionally dissolved in HOAc and freeze-dried to give the deprotected form of 9c.

Scheme 9

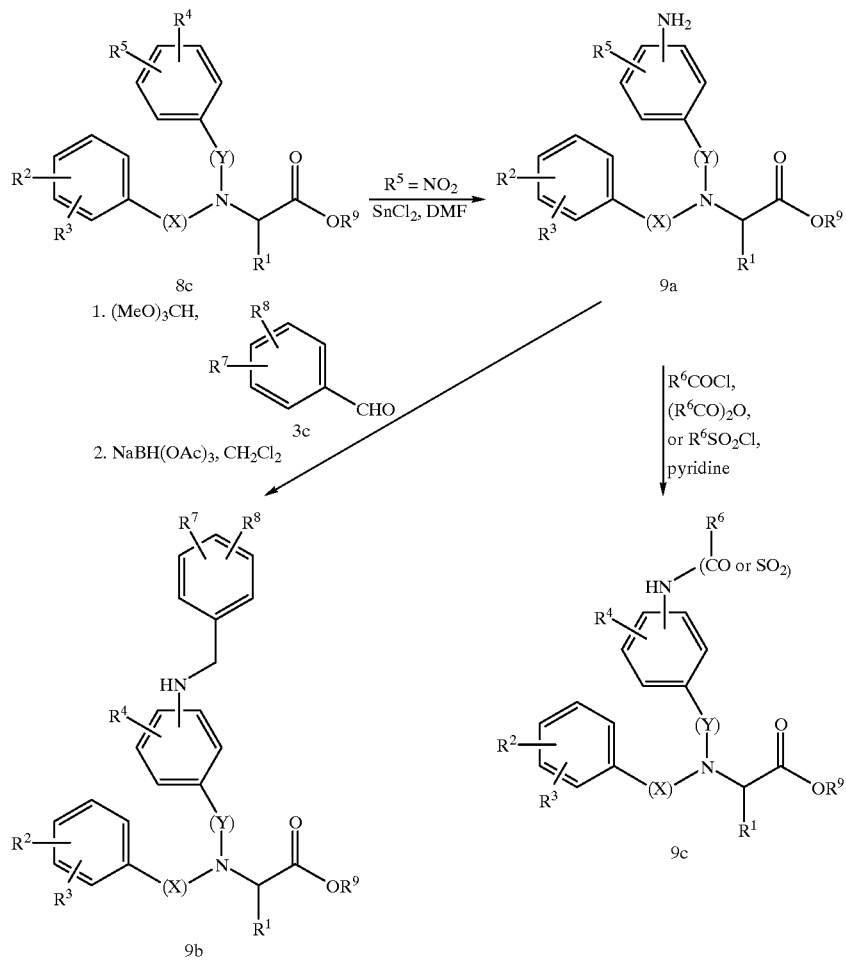

General Procedure For The Solution-Phase Synthesis Of Symmetrical N,N-Disubstituted Amino Amides And Their Dimers and Trimers Scheme 10. Step A A solution of 1 mmol of N-Cbz-protected amino acid 10a and the appropriate amine (ZH, 1 mmol), diamine (ZH$_2$, 0.5 mmol), or triamine (ZH$_3$ 0.33 mmol), was treated with 1.1 mmol of HOBt, 1.1 mmol of DIEA, and 2.1 mmol of EDCI in 3–6 mL of CH$_2$Cl$_2$ or DMF. [Alternatively, 1 mmol of the pentafluorophenyl ester or N-hydroxysuccinimide ester of 10a was mixed with the appropriate portion of amine (ZH), diamine (ZH$_2$), or triamine (ZH$_3$) in 3–6 mL of DMF.] The solution was stirred at room temperature under N$_2$ for 12–24 h, and EtOAc was added. The organic solution was washed with 5% aqueous citric acid, water, saturated NaHCO$_3$, and brine, dried over Na$_2$SO$_4$, and concentrated. The crude product was optionally purified by MPLC to afford amide 10b. Compound 10b was stirred in 30–80% TFA/CH$_2$Cl$_2$ for 1–3 h. The reaction mixture was concentrated to provide the TFA salt which was dissolved in CH$_2$Cl$_2$ or EtOAc and washed with aqueous NaOH or Na$_2$CO$_3$, dried over Na$_2$SO$_4$, and concentrated to give 10c as the free base.

Scheme 10, Step B

A solution of 1 mmol of amino acid ester 10c, 2.5–3 mmol of the appropriately substituted chloride or bromide 2c, and 2.5–3 mmol of an appropriate base such as DIEA, Na$_2$CO$_3$, or Cs$_2$CO$_3$ in 3–5 mL of DMF was heated at 50–100° C. under N$_2$ for 18–24 h. (For examples of 10c where n=2 or 3, the amounts of 2c and base were increased by two- or three-fold, respectively.) The reaction mixture was cooled and partitioned between water and EtOAc. The organic layer was washed three times with water and once with brine, dried over Na$_2$SO$_4$, and concentrated. The crude product was purified by MPLC to give pure amide 10d.

Alternatively, a solution of 1 mmol of amino acid ester 10c (n=1), 2.5–3 mmol of the appropriately substituted aldehyde 2a, and 2.5–3 mmol of borane-pyridine complex in 3–5 mL of DMF or EtOH was stirred at room temperature under N$_2$ for 3–5 days. (For examples of 10c where n=2 or 3, the amounts of 2c and borane-pyridine complex were increased by two- or three-fold, respectively.) The mixture was concentrated to dryness and was partitioned between water and CH$_2$Cl$_2$, washed with brine, dried over Na$_2$SO$_4$, and concentrated. The crude product was purified by MPLC to give pure amide 10d.

Scheme 10, Step C

For examples of 10d where R$^1$=CH$_2$CH$_2$CO$_2$-t-Bu or CH$_2$CO$_2$-t-Bu, 10d was stirred in 30–80% TFA/CH$_2$Cl$_2$ for 1–24 h. The reaction mixture was concentrated and optionally dissolved in HOAc and freeze-dried to give acid 10e.

Scheme 10, Step D

For examples of 10d where R$^1$ is equal to (CH$_2$)$_4$NHBoc, 10d was stirred in 30–80% TFA/CH$_2$Cl$_2$ for 1–24 h. The reaction mixture was concentrated and optionally dissolved in HOAc and freeze-dried to give amine 10f as the TFA salt which was optionally dissolved in CH$_2$Cl$_2$ or EtOAc. washed with aqueous NaOH or Na$_2$CO$_3$, dried over Na$_2$SO$_4$, and concentrated to give 10f as the free base.

Scheme 10, Step E

A solution of 1 mmol of 10f, 1–4 mmol of an appropriate base such as DIEA, and 1–2 mmol of the appropriately substituted cyclic anhydride 3e was stirred in CH$_2$Cl$_2$ or DMF under N$_2$ overnight. The resulting mixture was diluted with CH$_2$Cl$_2$ or EtOAc and washed with aqueous HCl, water, and brine, was dried over Na$_2$SO$_4$, and concentrated to provide acid 10g. Alternatively, 1 mmol of 10f, 1–4 mmol of an appropriate base such as DIEA, and 1–2 mmol of the appropriately substituted carboxylic acid anhydride (R$^{11}$CO)$_2$O or acid chloride R$^{11}$COCl was stirred in CH$_2$Cl$_2$ or DMF under N$_2$ overnight and worked up as above to provide 10h. Alternatively, 1 mmol of 8e, 1–4 mmol of an appropriate base such as DIEA, and 1–2 mmol of the appropriately substituted isocyanate R$^{12}$NCO was stirred in CH$_2$Cl$_2$ or DMF under N$_2$ overnight and worked up as above to provide 10i.

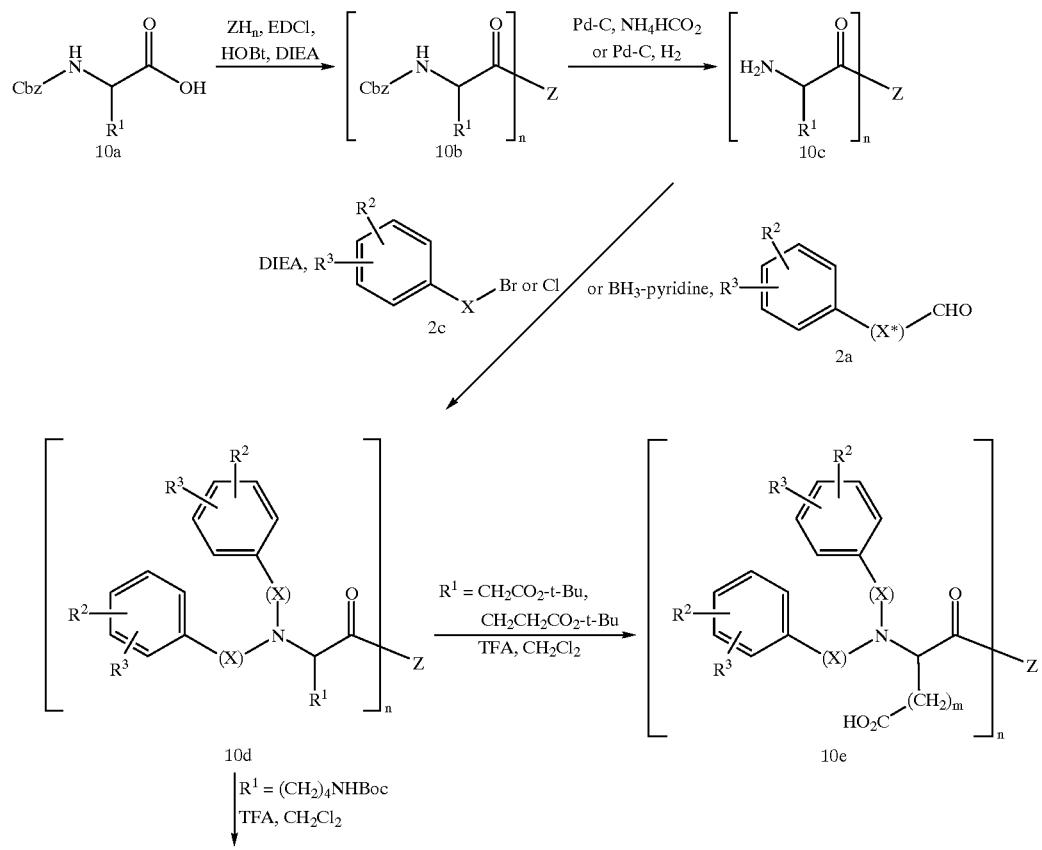

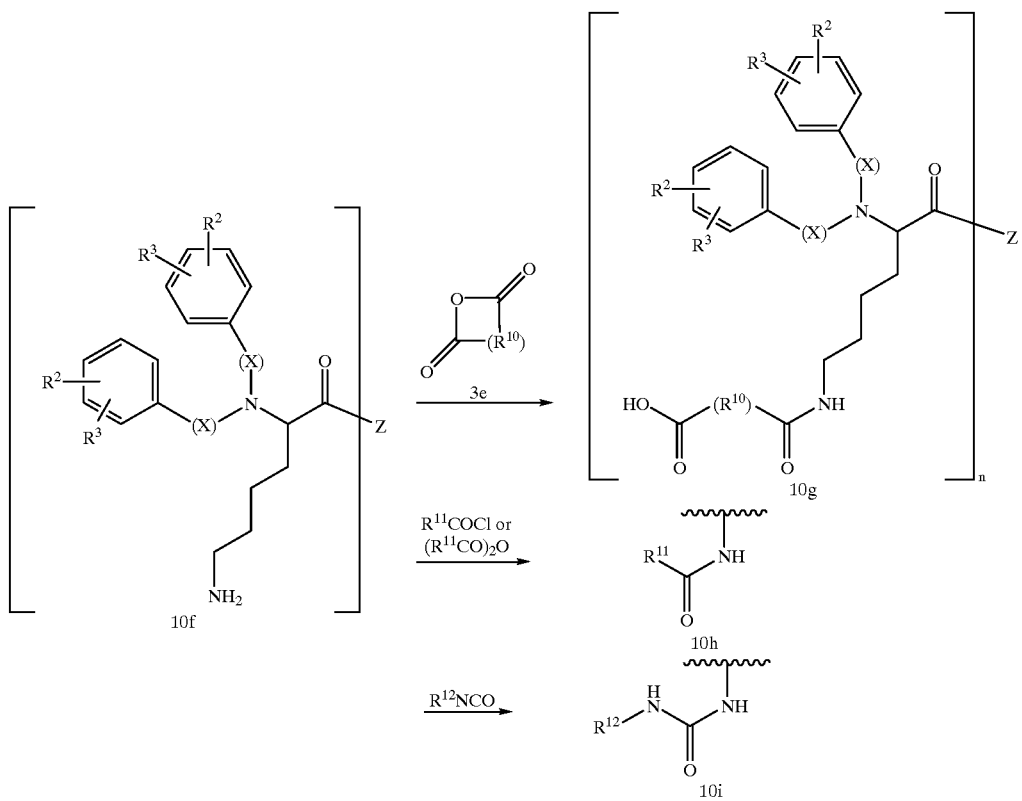

Scheme 11: General Procedure for the Solution Phase Synthesis of Symmetrical N,N-Disubstituted Amino Acids.

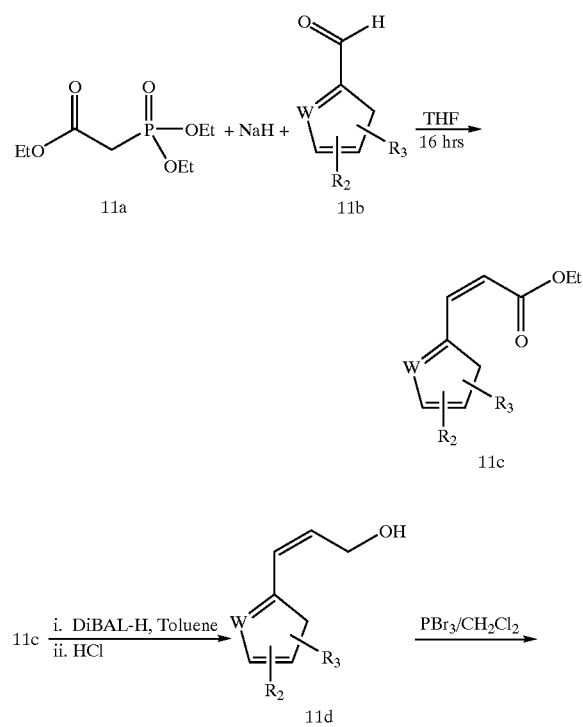

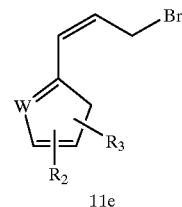

Sodium hydride (60% in mineral oil) is added to dry THF under nitrogen and stirred at 0–5° C. A THF solution of Triethylphosphonoacetate, (11a, 1 eq.) is added over about 10 min. The Ice-bath is removed and the mixture is stirred for about 10 min. A THF solution of a compound of 11b, 0.8 eq. is added over 5 min. and the reaction mixture is stirred for about 16 hours at room temperature. The reaction mixture is extracted into ethyl acetate and 5% $NaHCO_3$ solution. The ethyl acetate extract is washed with saturated NaCl solution, separated, dried over anhydrous $Na_2SO_4$ and concentrated. Chromatography, using EtOAc/Hexane (5:95) yields a product of the formula 11c. 1M DiBAL-H in toluene is added to a solution of 11c in toluene at 0° C. and stirred for about 16 hrs. The reaction mixture is extracted into EtOAc and 2M HCl. The EtOAc phase is washed with saturated NaCl solution and dried over anhydrous $Na_2SO_4$. Evaporation of the EtOAc layer gives the product of 11d.

A solution of PBr3 (0.5 eq.) is added slowly to a $CH_2Cl_2$ solution of 11d at 0° C. and the mixture is allowed to warm to room temperature and stirred for about 16 hrs. The reaction solution is extracted into $CH_2Cl_2$ and saturated $NaHCO_3$ solution. The $CH_2Cl_2$ solution is washed with water and dried over anhydrous $Na_2SO_4$ and concentrated. Chromatography with EtOAc/Hexane (5:95) yields the product of 11e.

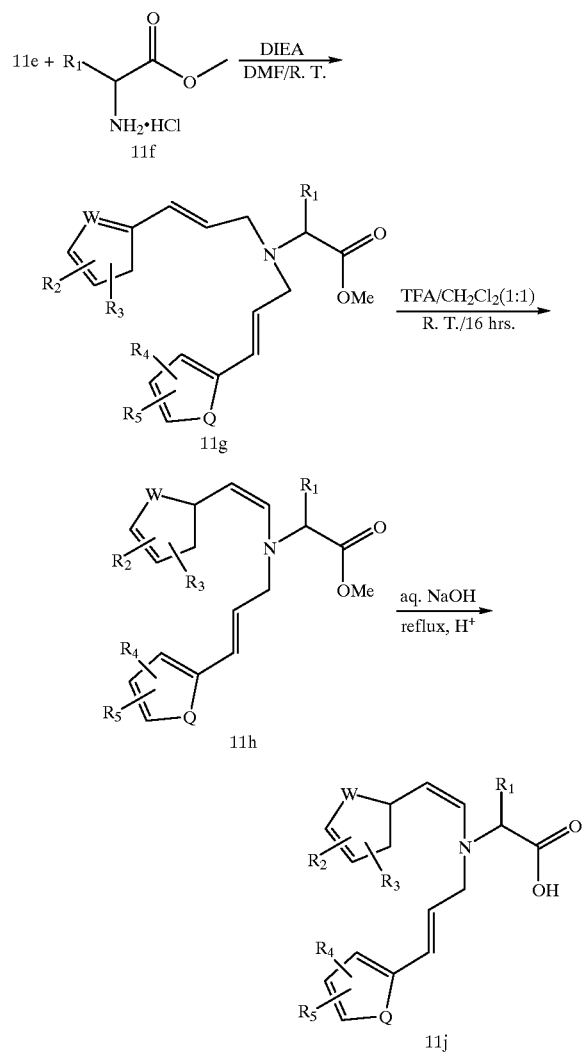

A DMF solution of 11e and 11f (0.85 eq.), and diisopropylethylamine (2 eq.) are stirred for 16 hrs. at room temperature under nitrogen. The reaction mixture is poured into a ice-water mixture and extracted with EtOAc. The organic phase is dried over anhydrous $Na_2SO_4$ and concentrated. Chromatography separates the symmetrical bis compound (11g) from the mono compound. using EtOAc/Hexane (10:90). Room temperature stirring of 11 g with TFA/$CH_2Cl_2$ (1:1) for about 16 hours gives 11h, which after heating with aqueous NaOH solution and final acidification yields 11j.

Scheme 12: Solution phase synthesis of alkynyl N,N-Disubstituted Amino Acids—General Procedure:

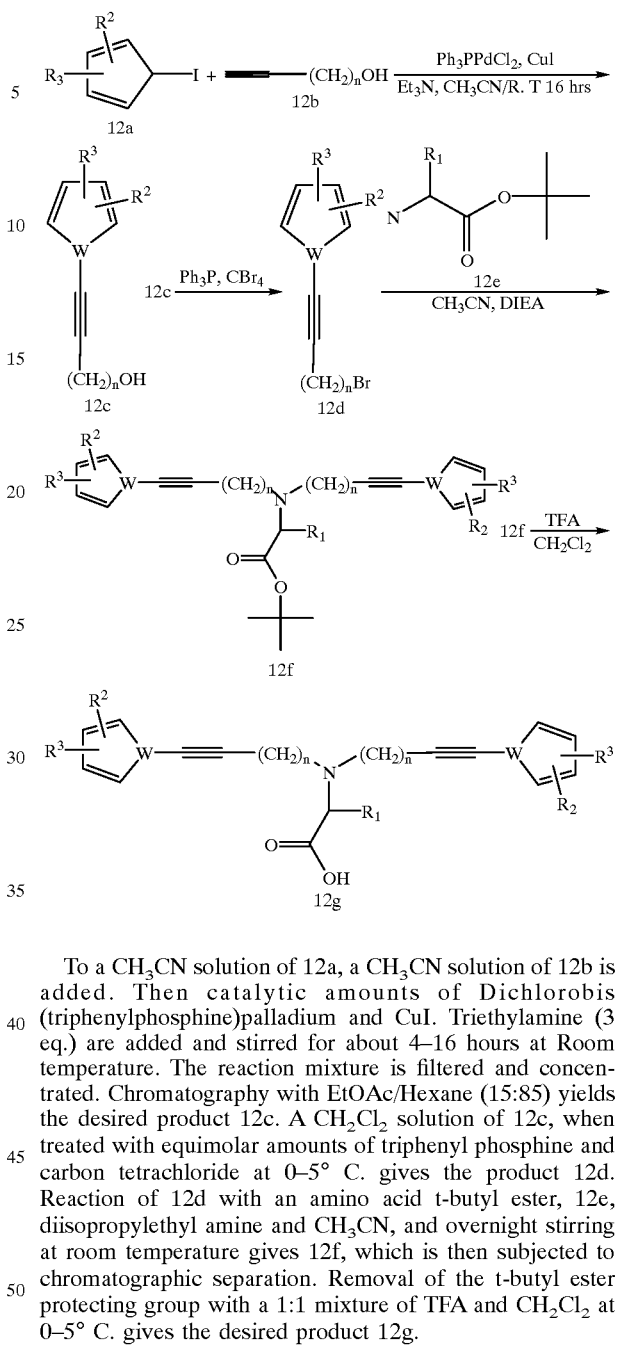

To a $CH_3CN$ solution of 12a, a $CH_3CN$ solution of 12b is added. Then catalytic amounts of Dichlorobis (triphenylphosphine)palladium and CuI. Triethylamine (3 eq.) are added and stirred for about 4–16 hours at Room temperature. The reaction mixture is filtered and concentrated. Chromatography with EtOAc/Hexane (15:85) yields the desired product 12c. A $CH_2Cl_2$ solution of 12c, when treated with equimolar amounts of triphenyl phosphine and carbon tetrachloride at 0–5° C. gives the product 12d. Reaction of 12d with an amino acid t-butyl ester, 12e, diisopropylethyl amine and $CH_3CN$, and overnight stirring at room temperature gives 12f, which is then subjected to chromatographic separation. Removal of the t-butyl ester protecting group with a 1:1 mixture of TFA and $CH_2Cl_2$ at 0–5° C. gives the desired product 12g.

This scheme is conducted as a Symmetrical synthesis by utilizing only one form of 12d. As shown, the ring consisting of substituents Q, R2, and R3 is the same as W, R4, and R5. Alternatively the synthetic scheme can be made Assymetrical by mixing at least two forms of a compound of the formula of 12d together prior to the coupling reaction.

Although the claimed compounds are useful as modulators of neutral shingomylenase, some compounds are more active than other.

The particularly preferred $R^2$ and $R^3$ are joined into one six member ring or methoxy.

The particularly preferred $R^4$ and $R^5$ are joined into one six member ring, or methoxy.

The particularly preferred W is —CH=CH— or —CH=N—.

The particularly preferred Q is —CH=CH— or —CH=N—.

The particularly preferred X are —CH=CH—CH$_2$— or —C≡C—(CH$_2$)$_n$, where n is 0–2.

The particularly preferred Y are —CH=CH—CH$_2$— or —C≡C—(CH$_2$)$_n$ where n is 0–2.

Pharmaceutically useful compositions comprising the compounds of the present invention, may be formulated according to known methods such as by the admixture of a pharmaceutically acceptable carrier. Examples of such carriers and methods of formulation may be found in Remington's Pharmaccutical Sciences. To form a pharmaceutically acceptable composition suitable for effective administration, such compositions will contain an effective amount of the compound of the present invention.

Therapeutic or diagnostic compositions of the present invention are administered to an individual in amounts sufficient to treat or diagnose disorders in which inhibition of neutral sphingomyelinase activity is indicated. Examples of diseases or conditions known to be, or suspected of being mediated by neutral sphingomyelinase include but are not limited to rheumatoid arthritis, gastrointestinal inflammatory disease, asthma, psoriasis, B cell lymphoma, and T cell lymphoma. The effective amount of a compound of the present invention may vary according to a variety of factors such as the individual's condition, weight, sex and age. Other factors include the mode of administration. The pharmaceutical compositions of the present invention may be provided to the individual by a variety of routes including, but not limited to subcutaneous, intramuscular, intraveinous, topical, transdermal, oral and any other parenteral or non-parenteral route.

The term "chemical derivative" describes a molecule that contains additional chemical moieties that are not normally a part of the base molecule. Such moieties may improve the solubility, half-life. absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds disclosed herein may be used alone at appropriate dosages defined by routine testing in order to obtain optimal inhibition of neutral sphingomyelinase while minimizing any potential toxicity. In addition, co-administration or sequential administration of other agents may be desirable.

The present invention also has the objective of providing suitable topical, transdermal, oral, systemic and parenteral pharmaceutical formulations for use in the novel methods of treatment of the present invention. Compositions containing compounds of the present invention as the active ingredient for use in the modulation of neutral sphingomyelinase can be administered in a wide variety of therapeutic dosage forms in conventional vehicles for administration. For example, the compounds or modulators can be administered in such oral dosage forms as tablets, capsules (each including timed release and sustained release formulations), pills, powders, granules, elixirs, tinctures, solutions, suspensions, syrups and emulsions, or by transdermal delivery or injection. Likewise, they may also be administered in intravenous (both bolus and infusion), intraperitoneal, subcutaneous, topical with or without occlusion, transdermal, or intramuscular form, all using forms well known to those of ordinary skill in the pharmaceutical arts. The compounds of the present invention may be delivered by a wide variety of mechanisms, including but not limited to, transdermal delivery, or injection by needle or needle-less injection means. An effective but non-toxic amount of the compound desired can be employed as a neutral sphingomyelinase-modulating agent.

The daily dosage of the products may be varied over a wide range from 0.01 to 1,000 mg per patient, per day. For oral administration, the compositions are preferably provided in the form of scored or un-scored tablets containing 0.01, 0.05, 0.1. 0.5, 1.0. 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0001 mg/kg to about 100 mg/kg of body weight per day. The range is more particularly from about 0.001 mg/kg to 10 mg/kg of body weight per day. The dosages of the compounds of the present invention are adjusted when combined to achieve desired effects. On the other hand, dosages of these various agents may be independently optimized and combined to achieve a synergistic result wherein the pathology is reduced more than it would be if either agent were used alone.

Advantageously, compounds or modulators of the present invention may be administered in a single daily dose, or the total daily dosage may be administered in divided doses of two, three or four times daily. Furthermore, compounds or modulators for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds or modulators of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

In the methods of the present invention, the compounds or modulators herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form. e.g., alcoholic solutions, topical cleansers, cleansing creams, skin gels, skin lotions, and shampoos in cream or gel formulations.

The compounds or modulators of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidyicholines.

Compounds of the present invention may also be delivered by the use of monoclonal antibodies as individual carriers to which the compound molecules are coupled. The compounds or modulators of the present invention may also be coupled with soluble polymers as targetable drug carriers. Such polymers can include polyvinyl-pyrrolidone, pyran copolymer, polyhydroxypropylmethacryl-amidephenol, polyhydroxy-ethylaspartamideplhenol, or polyethyleneoxidepolylysine substituted with palmitoyl residues. Furthermore, the compounds or modulators of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels, and other suitable polymers known to those skilled in the art.

For oral administration, the compounds or modulators may be administered in capsule, tablet, or bolus form or alternatively they can be mixed in the animals feed. The capsules, tablets, and boluses are comprised of the active ingredient in combination with an appropriate carrier vehicle such as starch, talc, magnesium stearate, or di-calcium phosphate. These unit dosage forms are prepared by intimately mixing the active ingredient with suitable finely-powdered inert ingredients including diluents, fillers, disintegrating agents, and/or binders such that a uniform mixture is obtained. An inert ingredient is one that will not react with the compounds or modulators and which is non-toxic to the animal being treated. Suitable inert ingredients include starch, lactose, talc, magnesium stearate, vegetable gums and oils, and the like. These formulations may contain a widely variable amount of the active and inactive ingredients depending on numerous factors such as the size and type of the animal species to be treated and the type and severity of the infection. The active ingredient may also be administered as an additive to the feed by simply mixing the compound with the feedstuff or by applying the compound to the surface of the feed. Alternatively the active ingredient may be mixed with an inert carrier and the resulting composition may then either be mixed with the feed or fed directly to the animal. Suitable inert carriers include corn meal, citrus meal, fermentation residues, soya grits, dried grains and the like. The active ingredients are intimately mixed with these inert carriers by grinding, stirring, milling, or tumbling such that the final composition contains from 0.001 to 5% by weight of the active ingredient.

The compounds or modulators may alternatively be administered parenterally via injection of a formulation consisting of the active ingredient dissolved in an inert liquid carrier. Injection may be either intramuscular, intraruminal, intratracheal, or subcutaneous, either by needle or needle-less means. The injectable formulation consists of the active ingredient mixed with an appropriate inert liquid carrier. Acceptable liquid carriers include the vegetable oils such as peanut oil, cottonseed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 10% by weight of the active ingredient.

Topical application of the compounds or modulators is possible through the use of a liquid drench or a shampoo containing the instant compounds or is modulators as an aqueous solution or suspension. These formulations (generally contain a suspending agent such as bentonite and normally will also contain an antifoaming agent. Formulations containing from 0.005 to 10% by weight of the active ingredient are acceptable. Preferred formulations are those containing from 0.01 to 5% by weight of the instant compounds or modulators.

The compounds of Formula I may be used in pharmaceutical compositions to treat patients (humans and other mammals) with disorders or conditions associated with the activity or hyperactivity of neutral sphingomyelinase. The compounds can be administered in the manner of the commercially available product or by any oral or parenteral route (including but not limited to, intravenous, intraperitoneal, intramuscular, subcutaneous, dermal patch), where the preferred route is by injection. When the method of administration is intravenous infusion, compound of Formula I may be administered in a dose range of about 0.01 to 1 mg/kg/min. For oral administration, the dose range is about 0.1 to 100 mg/kg.

The pharmaceutical compositions can be prepared using conventional pharmaceutical excipients and compounding techniques. Oral dosage forms may be used and are elixirs syrups, capsules, tablets and the like. Where the typical solid carrier is an inert substance such as lactose, starch, glucose, methylcellulose, magnesium stearate, dicalcium phosphate, mannitol and the like; and typical liquid oral excipients include ethanol, glycerol, water and the like. All excipients may be mixed as needed with disintegrants, diluents, granulating agents, lubricants, binders and the like using conventional techniques known to those skilled in the art of preparing dosage forms. Parenteral dosage forms may be prepared using water or another sterile carrier.

Typically the compounds of Formula I are isolated as the free base, however when possible pharmaceutically acceptable salts can be prepared. Examples of such salts include hydrobromic, hydroiodic, hydrochloric, perchloric, sulfuric, maleic, fumaric, malic, tartaric, citric, benzoic, mandelic, methanesulfonic, hydroethanesulfonic, benzenesulfonic, oxalic, pamoic, 2-naphthalenesulfonic, p-toluenesulfonic, cyclohexanesulfamic and saccharic.

In order to illustrate the invention the following examples are included. These examples do not limit the invention. They are only meant to suggest a method of practicing the invention. Those knowledgeable in chemical synthesis and the treatment of neutral sphingomyelinase related disorders may find other methods of practicing the invention. However those methods are deemed to be within the scope of this invention.

PREPARATIVE EXAMPLES

Unless otherwise noted, materials used in the examples were obtained from commercial suppliers and were used without further purification. Elemental analyses were performed by Quanititative Technologies, Inc. (QTI), PO Box 470, Salem Industrial Park, Bldg #5, Whitehouse, N.J. 08888-0470. Analytical thin layer chromatography (TLC) was done with Merck Silica Gel 60 $F_{254}$ plates (250 micron). Medium pressure liquid chromatography (MPLC) was done with Merck Silica Gel 60 (230–400 mesh).

Example 1

The starting reagent for 11b was 1-Naphthaldehyde, and substituting the appropriate amino acids or the appropriate amino acid derivative for 11f in scheme 11 yielded the compounds of Table 1.

TABLE 1

| Cmpd | Amino Acid Precursor (11f) | $R_1$ | Z | $M^+$ |
|---|---|---|---|---|
| 1 | L-Serine | $CH_2OH$ | OH | 438 |
| 2 | L-Alanine | Methyl | OH | 422 |
| 3 | L-Isoleucine | $CH(CH_3)C_2H_5$ | OH | 464 |
| 4 | L-Tryptophan | $CH_2$Indole | OH | 537 |
| 5 | 1-Amino-1-carboxycyclopentane | Cyclopentyl | OH | 462 |
| 6 | 3-Aminoisobutyric acid | $CH_2CH(CH_3)$ | OH | 436 |
| 7 | L-Asp-L-Phe methyl ester | $CH_2CO_2H$ | N-Phe Me ester | 627 |
| 8 | 3-Amino-4-carbethoxypyrazole | 5-Amino-4-pyrazoyl | Oet | 488 |
| 9 | L-Ala-L-Ala | Methyl | N-Ala | 493 |
| 10 | L-Thr | $CH(OH)CH_3$ | OH | 452 |
| 11 | L-Gly | H | OH | 408 |
| 12 | L-Ser Na salt | $CH_2OH$ | ONa | 437 |

Substituting, Quinoline-4-carboxaldehyde for 1-Naphtaldehyde as compound 11b in the above process and employing L-Alaninc as the amino acid precursor as compound 11f yields compound 13 ($M^+$=424), of the structure

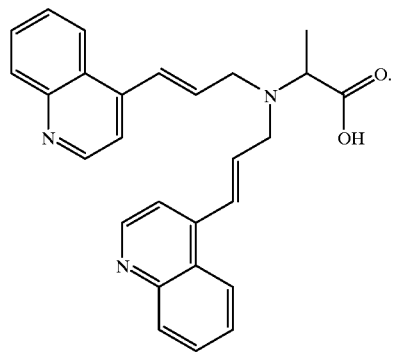

Substituted Amino Acids as Sphingomyelinase Inhibitors—Quaternary Salts

Three quaternary compounds were synthesized by adding $CH_3I$/acetone to the appropriate amine. Compound 14 was prepared from the serine-derived carboxylic acid (compound 1). The corresponding free acid (cmpd 16) was prepared by hydrolysis of the quaternary salt of the t-butyl ester. The alanine derived quaternary salt (cmpd 15) was prepared by treatment of the t-butyl ester directly with $CH_3I$/acetone.

TABLE 2

| Cmp | $R_1$ | z' |
|---|---|---|
| 14 | $CH_2OH$ | $CH_3$ |
| 15 | $CH_3$ | t-Butyl |
| 16 | $CH_2OH$ | H |

Example 2

Scheme 12 was employed, either 1-iodonaphthalene or 4-Iodoanisole as compound 12a and propargyl alcohol as 12b. Substituting L-alanine t-butyl ester or a protected serine derivative for 12e in scheme 12 yielded the compounds of Table 3.

TABLE 3

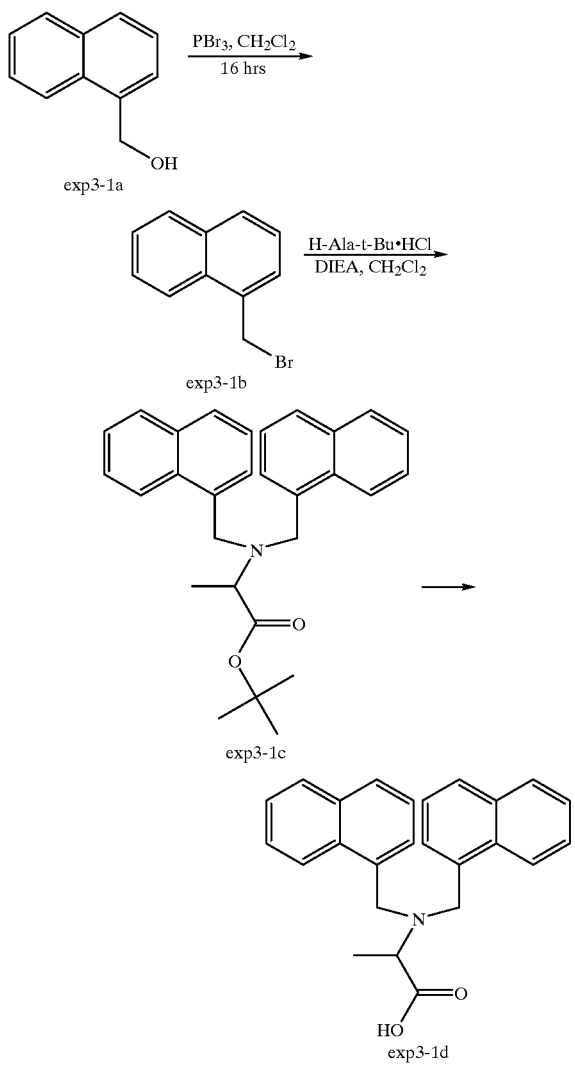

| Cmpd | W | $R_2/R_3$ | N | $R_1$ | $M^+$ |
|---|---|---|---|---|---|
| 17 | —CH=CH— | Six member ring | 1 | $CH_3$ | 418 |
| 18 | —CH=CH— | Six member ring | 1 | $CH_2OH$ | 434 |
| 19 | —CH=CH— | Methoxy | 1 | $CH_3$ | 378 |

Example 3

Compounds were synthesized using scheme 7 as described. The first reaction illustrates the generation of the bromide substituted naphthalene compound exp3-1b.

A $CH_2Cl_2$ solution of 1-Naphthalenemethanol (exp1a) was stirred with a 1M solution of $PBr_3$ in $CH_2Cl_2$ at room temperature for about 16 hrs. The reaction solution was extracted into EtOAc and washed with saturated NaCl solution. The organic phase was dried and concentrated to give exp3-1b in quantitative yield (99%). Coupling of exp-1b with EI-Ala-t-Bu ester HCl in the presence of diisopropylethylamine, using $CH_2Cl_2$ as solvent gave exp-1c after chromatography in 32% yield. Treatment of exp-1c with $TFA/CH_2Cl_2(1:1)$ at 5–15° C. gave exp-1d, compound 20 ($M^+=370$), as a TFA salt in quantitative yield.

Substitution of the appropriate 1-naphthalene alkyl halide for exp-1b and substitution of the appropriately protected serine derivative for H-Ala-t-Bu ester HCl gave the compounds in Table 3.

TABLE 3

| Cmpd | $(CH_2)n$ | $M^+$ |
|---|---|---|
| 21 | 1 | 386 |
| 22 | 2 | 414 |
| 23 | 3 | 442 |

Example 4

Synthesis of Compound 1

Serine, N-[(2E)-3-(1-Naphthalenyl)-2-propenyl]-N-[3-(1-naphthalenyl)-2-propenyl]—

The title compound was synthesized utilizing scheme 11 as described herein. Specific compounds are noted as the compound corresponding to the scheme depiction.

Sodium hydride (60% in mineral oil) was added to dry TIF under nitrogen and stirred at 0–5° C. A THF solution of Triethylphosphonoacetatc, (11a,1 eq.) was added over about 10 minutes. The Ice-bath was removed and the mixture was stirred for about 10 min. A THF solution of 1-Naphthaldehyde (11b,0.8 eq.) was added over 5 min. and the reaction mixture was stirred for about 16 hours at room temp. The reaction mixture was extracted into ethyl acetate and 5% $NaHCO_3$ solution. The ethyl acetate extract was washed with saturated NaCl solution, separated, dried over anhydrous $Na_2SO_4$ and concentrated. Chromatography using EtOAc/Hexane (5:95) gave a pale yellow oil of 2-propenoic acid, 3-(1-naphthalenyl)-, ethyl ester, (2Z)—(11c, 99%).

1M DiBAl-H in toluene was added to a solution of 11c in toluene at 0° C. and stirred for about 16 hours. The reaction mixture was extracted into EtOAc and 2M HCl. The EftOAc phase was washed with saturated NaCl solution and dried over anhydrous $Na_2SO_4$. Evaporation of the EtOAc layer gave the product 2-propen-1-ol, 3-(1-naphthalenyl)-, (2Z)—(11d, 95%).

A solution of $PBr_3$ (0.5 eq.) was added slowly to a $CH_2Cl_2$ solution of 11d at 0° C. and the mixture was allowed to warm to room temperature and stirred for about 16 hours.

The reaction solution was extracted into $CH_2Cl_2$ and saturated $NaHCO_3$ solution. The $CH_2Cl_2$ solution was washed with water and dried over anhydrous $Na_2SO_4$ and concentrated. Chromatography with EtOAc/Hexane (5:95) gave a yellow oil of naphthalene, 1-[(1Z)-3-bromo-1-propenyl]— (11e, 90%).

A DMF solution of 1.73g (7 mmol) 11e and 1.27g (6 mmol) of tert-butly serine methyl ester (11f), and 2 ml of diusopropylethylamine were stirred for 16 hours at room temperature under nitrogen. The reaction mixture was poured into a ice-water mixture and extracted with EtOAc. The organic phase was dried over anhydrous $Na_2SO_4$ and concentrated. Chromatography separated the symmetrical bis compound from the mono compound, using EtOAc/Hexane (10:90), in about 40% yield. Room temperature stirring of 0.794g of the bis compound with $TFA/CH_2Cl_2$ (5 ml of each) for about 16 hours gave serine, N-[(2E)-3-(1-naphthalenyl)-2-propenyl]-N-[3-(1-naphthalenyl)-2-propenyl]-, methyl ester (11h), which after heating with aq. NaOH solution and final acidification gave the title compound (0.079g) ($M^+$=438) as a light brown solid.

Example 5

Synthesis of Compound 2

Alanine, N,N-Bis[(2E)-3-(1-naphthalenyl)-2-propenyl]—

This compound was synthesized using the starting material from example 4, and substituting the following conditions starting at compound 11f.

A DMF solution of 3.2g (12.9 mmol) 11e and 1.17g (8.1 mmol) of tert-butyl alanine methyl ester (11f) and 2 ml of diisopropylethylamine were stirred for 16 hours at room temperature under nitrogen. The reaction mixture was poured into a ice-water mixture and extracted with EtOAc. The organic phase was dried over anhydrous $Na_2SO_4$ and concentrated. Chromatography separated the symmetrical bis compound from the mono compound, using EtOAc/Hexane (10:90). Room temperature stirring of 1.151 g of the bis compound with $TFA/CH_2Cl_2$ (5 ml of each) for about 16 hours gave alanine, N,N-bis[(2E)-3-(1-naphthalenyl)-2-propenyl]—, methyl ester (11h), which after heating with aq. NaOH solution and final acidification gave the title compound (0.145 g).

Example 6

Synthesis of Compound 17

Alanine, N,N-Bis[3-(1-naphthalenyl)-2-propynyl]—

The title compound was synthesized utilizing scheme 12 as described herein. Specific compounds are noted as the compound corresponding to the scheme depiction.

5g (21 mmol) 1-Iodonaphthalene (12a) was disolved in $CH_3CN$ and combined with a $CH_3CN$ solution of 1.73 g (3 mmol) Propargyl alcohol (12b). Than catalytic amounts of Dichlorobis(triphenylphosphinc)palladium and CuI. Triethylamine (10 ml) were added and stirred for about 4 hours at room temperature. The reaction mixture was filtered and concentrated. Chromatography with EtOAc/Hexane (15:85) gave 3.1 g 2-propyn-1-ol, 3-(1-naphthalenyl)—(12c) as a brown oil (99% yield). A $CH_2Cl_2$ solution of 0.81 g 12c, when treated with equimolar amounts of triphenyl phosphine (1.31 g) and carbon tetrachloride (1.66g) at 0–5° C. gave naphthalene, 1-(3-bromo-1-propynyl)—(12d) in almost quantitative yields. Upon coupling, reaction of 1.20 g of 12d with 0.908 g L-alanine t-butyl ester, diisopropylethyl amine and $CH_3CN$, and overnight stirring at room temperature gave 0.403 g 12e after chromatographic separation. Removal of the t-butyl ester protecting group with a 1:1 mixture of TFA and $CH_2Cl_2$ at 0–5° C. gave 0.171 g of the title compound ($M^+$=418).

Example 7

BIOLOGICAL Activity

Neutral sphingomyelinase is an enzyme that cleaves sphingomyelin to yield ceramide and phosphocholine. The assay used in the present invention utilizes radiolabeled sphingomyelin that has a $^{14}C$ label on the phosphocholine portion of the molecule. After cleavage, an extraction separates the labeled, water-soluble phosphocholine from the intact substrate and the ceramide.

Lysate (Enzyme) Preparation: U937 cells (ATCC CRL-1593.2) are maintained in RPMI 1640 with 10% FBS (Gibco) at 37 C and 5% CO2. Cell lysates are made by nitrogen cavitation of harvested cells in Buffer A (20 mM Tris, pH 7.4, 250 mM sucrose, 10 mM EGTA, 10 ug/ml leupeptin, 1 mM PMSF, 2 M pepstatin). Lysates are flash frozen and stored at −40 C.

Substrate Preparation: N-methyl-$^{14}C$-sphingomyelin (specific activity 50 mCi/mM) and phosphatidylinositol are evaporated under a stream of nitrogen and resuspended at an equimolar concentration of 0.1 mM in water with 0.5% Triton X-100. The solution is vortexed for 30 minutes and then sonicated for 30 minutes.

Sphingomyelinase Assay: The reaction mixture contains 25 ul 2X Tris Mg buffer (200 mM Tris-HCl, pH 7.5. 160 mM MgCl), 10 ul $^{14}C$-sphingomyelin substrate, 10 ul lysate (enzyme) and 5 ul test compound or vehicle for a final volume of 50 l. The assays are carried out in 1.5 ml microcentriftige tubes and are incubated for 1 hour at 37. The reaction is stopped with 30 l of water and 175 l chloroform/methanol (2:1, v:v). The tubes arc vortexed vigorously, centrifuged for 5 minutes in a microfuge at maximum speed and 50 l of the upper, aqueous phase is counted in a liquid scintillation counter. Alternatively, the assay may be set up in wells of a 96-well PCR plate in identical proporations to a total volume of 50 l. Then the plates are incubated at 37 C incubator for 1 hour. $H_2O$ (30 l) is added to all plates and the plates are again incubated for 1 hour. Chloroform-methanol (2:1) is added in a volume of 175 l followed by vigorous mixing. The plates are sealed with adhesive covers and centrifuged at 3000 rpm for 10 minutes at 5 C. The plates are uncovered and 50 l of upper, aqueous phase is transferred to a Flashplate™(NEN) scintillation proximity assay plate. The Flashplates are dried overnight, sealed, and counted using a Topcount scintillation counter.

Compounds that are antagonists of neutral sphingomyelinase are reported as a positive value for inhibition in Table 4. For compounds to which an IC50 was not determined, a percentage of enzyme inhibition is reported for the highest concentration tested (100 uM).

TABLE 4

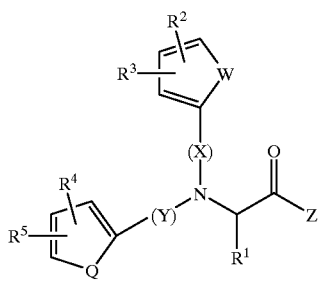

| Cmp | W/Q | R2/R3 | R4/R5 | X/Y | R1 | Z | IC50 |
|---|---|---|---|---|---|---|---|
| 2 | —CH=CH— | ring | ring | —CH=CH—CH$_2$— | Ala | OH | 2.8 uM |
| 1 | —CH=CH— | ring | ring | —CH=CH—CH$_2$— | Ser | OH | 1.8 uM |
| 14 | —CH=CH— | ring | ring | —CH=CH—CH$_2$— | Ser | O—CH$_3$ | 19 uM |
| 15 | —CH=CH— | ring | ring | —CH=CH—CH$_2$— | Ala | OH | 28 uM |
| 16 | —CH=CH— | ring | ring | —CH=CH—CH$_2$— | Ser | OH | 24% |
| 10 | —CH=CH— | ring | ring | —CH=CH—CH$_2$— | Thr | OH | 21% |
| 24 | —CH=N— | ring | ring | —CH=CH—CH$_2$— | Ala | Tert-butoxy | <5% |
| 17 | —CH=CH— | ring | ring | —C≡C—CH$_2$— | Ala | OH | 10 uM |
| 19 | —CH=CH— | Methoxy | Methoxy | —C≡C—CH$_2$— | Ala | OH | 27% |
| 23 | —CH=CH— | ring | ring | —(CH$_2$)$_3$— | Ser | OH | 89 uM |
| 20 | —CH=CH— | ring | ring | —CH$_2$— | Ala | OH | <5% |
| 21 | —CH=CH— | ring | ring | —CH$_2$— | Ser | OH | <5% |
| 22 | —CH=CH— | ring | ring | —(CH$_2$)$_2$— | Ser | OH | <5% |
| 25 | —CH=CH— | ring | ring | —(CH$_2$)$_2$— | Ala | OH | <5% |
| 18 | —CH=CH— | ring | ring | —C≡C—CH$_2$— | Ser | OH | <5% |
| 13 | —CH=N— | ring | ring | —CH=CH—CH$_2$ | Ala | OH | <5% |

What is claimed is:

1. A method for inhibiting neutral sphingomyelinase, comprising contacting neutral sphingomyelinase with a neutral sphingomyelinase inhibiting amount of a compound of Formula I:

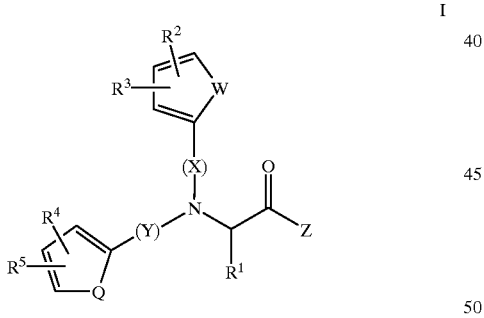

wherein:

$R^1$ is the side chain of an amino acid, wherein said amino acid is selected from the group consisting of natural α-amino acids of L configuration, natural α-amino acids of D-configuration, α-aminoadipic acid, 4-aminobutanoic acid, 6-aminohexanoic acid, α-aminosuberic acid, 5-aminopentanoic acid, p-aminophenylalanine, α-aminnopimelic acid, γ-carboxyglutamic acid, p-carboxyphenylalanine, carnitine, citrulline, α,β-diaminopropionic acid, α,γ-dianmiinobutyric acid, homocitrulline, homoserine, and statine, where if said side chain contains a protectable group, that group may be protected with a member of the group consisting of succinyl, glutaryl, 3,3-dimethylglutaryl, $C_{1-5}$alkyl, $C_{1-5}$alkoxycarbonyl, acetyl, N-(9-fluorenylmethoxycarbonyl), trifluoroacetyl, omega-carboxy$C_{1-5}$alkylcarbonyl, t-buroxycarbonyl, benzyl, benzyloxycarbonyl, 2-chlorobenzyloxycarbonyl, phenylsulfonyl, ureido, t-butyl, cinnamoyl, trityl, 4-methyltrityl, 1-(4,4-dimethyl-2,6-dioxocyclohexylidene)ethyl, tosyl, 4-methoxy-2,3,6-trimethylbenzenesulfonyl, phenylureido, and substituted phenylureido (where the phenyl substituents are phenoxy, halo, $C_{1-5}$alkoxycarbonyl);

$R^2$ and $R^3$
are taken together to form a six-membered aromatic ring which is fused to the depicted ring, or,
are independently selected from the group consisting of hydrogen, $C_{1-5}$ alkyl, $C_{1-5}$ alkoxy, hydroxy, halo, trifluoromethyl, nitro, amino, phenyl, phenoxy, phenyl$C_{1-5}$alkyl, phenyl $C_{1-5}$alkoxy,
substituted phenyl (where the substituents are selected from $C_{1-5}$alkyl, $C_{1-5}$ alkoxy, hydroxy, halo, trifluoromethyl, nitro, nitrile, and amino),
substituted phenoxy (where the substituents are selected from $C_{1-5}$ alkyl, $C_{1-5}$ alkoxy, hyydroxy, halo, trifluoromethyl, nitro, nitrile, and amino),
substituted phenyl$C_{1-5}$alkyl (where the substituents are selected from $C_{1-5}$ alkyl, $C_{1-5}$ alkoxy, hydroxy, halo, trifluoromethyl, nitro, nitrile, and amino),
substituted phenyl$C_{1-5}$alkoxy (where the substituents are selected from $C_{1-5}$ alkyl, $C_{1-5}$ alkoxy, hydroxy, halo, trifluoromethyl, nitro, nitrile, and amino), and
substituted amino (where the substituents are selected from one or more members of the group consisting of $C_{1-5}$alkyl, halosubstituted$C_{1-5}$alkyl, $C_{1-5}$alknyl, $C_{1-5}$alkenyl, phenyl, phenyl$C_{1-5}$alkyl, $C_{1-5}$alkylcarbonyl, halo substituted $C_{1-5}$alkylcarbonyl, carboxy$C_{1-5}$alkyl, $C_{1-5}$alkoxy$C_{1-5}$alkyl, cinnamoyl, naphthylcarbonyl, furylcarbonyl, pyridylcarbonyl, $C_{1-5}$alkylsulfonyl, phenylcarbonyl, phenyl$C_{1-5}$alkylcarbonyl, phenylsulfonyl, phenyl$C_{1-5}$alkylsulfonyl substituted phenylcarbonyl, substituted phenyl$C_{1-5}$alkylcarbonyl, substituted phenylsulfonyl, substituted phenyl$C_{1-5}$alkylsulfonyl, substituted phenyl, and substituted phenyl$C_{1-5}$alkyl [where the aromatic phenyl, phenyl$C_{1-5}$alkyl, phenylcarbonyl, phenyl$C_{1-5}$alkylcarbonyl, phenylsulfonyl, and phenyl$C_{1-5}$alkylsulfonyl substitutents are independently selected from one to five members of the group consisting of $C_{1-5}$alkyl, $C_{1-5}$alkoxy, hydroxy, halogen, trifluoromethyl, nitro, nitrile, and amino]);

$R^4$ and $R^5$
are taken together to form a six-membered aromatic ring which is fused to the depicted ring, or,
are independently selected from the group consisting of hydrogen, $C_{1-5}$ alkyl, $C_{1-5}$ alkoxy, hydroxy, halo, trifluoromethyl, nitro, amino, pheny), phenoxy, pbenyl$C_{1-5}$alkyl, phenyl $C_{1-5}$alkoxy,
substituted phenyl (where the substituents are selected from $C_{1-5}$alkyl, $C_{1-5}$ alkoxy, hydroxy, halo, trifluoromethyl, nitro, nitrile, and amino),
substituted phenoxy (where the substituents are selected from $C_{1-5}$ alkyl, $C_{1-5}$ alkoxy, hydroxy, halo, trifluoromethyl, nitro, nitrite, and amino),
substituted phenyl$C_{1-5}$alkyl (where the substituents are selected from $C_{1-5}$ alkyl, $C_{1-5}$ alkoxy, hydroxy, halo, trifluoromethyl, nitro, nitrile, and amino),
substituted phenyl$C_{1-5}$alkoxy (where the substituents are selected from $C_{1-5}$ alkyl, $C_{1-5}$ alkoxy, hydroxy, halo, tifluoromethyl, nitro, nitrite, and amino), and
substituted amino (where the substituents are selected from one or more members of the group consisting of $C_{1-5}$alkyl, halosubstituted$C_{1-5}$alkyl, $C_{1-5}$alknyl, $C_{1-5}$alkenyl, phenyl, phenyl$C_{1-5}$alkyl, $C_{1-5}$alkylcarbonyl, halo substituted $C_{1-5}$alkylcarbonyl, carboxy$C_{1-5}$alkyl, $C_{1-5}$alkoxy$C_{1-5}$alkyl, cinnamoyl, naphthylcarbonyl, furylcarbonyl, pyridylcarbonyl, $C_{1-5}$alkylsulfonyl, phenylcarbonyl, phenyl$C_{1-5}$alkylcarbonyl, phenylsulfonyl, phenyl$C_{1-5}$alkylsulfonyl substituted phenylcarbonyl, substituted phenyl$C_{1-5}$alkylcarbonyl, substituted phenylsulfonyl, substituted phenyl$C_{1-5}$alkylsulfonyl, substituted phenyl, and substituted phenyl$C_{1-5}$alkyl [where the aromatic phenyl, phenyl$C_{1-5}$alkyl, phenylcarbonyl, phenyl$C_{1-5}$alkylcarbonyl, phenylsulfonyl, and phenyl$C_{1-5}$alkylsulfonyl substitutents are independently selected from one to five members of the group consisting of $C_{1-5}$alkyl, $C_{1-5}$alkoxy, hydroxy, halogen, trifluoromethyl, nitro, nitrile, and amino]);

W is selected from the group consisting of —CH=CH—,
Q is selected from the group consisting of —CH=CH—,
X is selected from the group consisting of carbonyl, $C_{1-5}$alkyl, $C_{1-5}$alkenyl, $C_{1-5}$alkenylcarbonyl, $C_{2-5}$alkynyl, $C_{2-5}$alkynylcarbonyl and $(CH_2)_m$—C(O)— where m is 2–5;
Y is selected from the group consisting of carbonyl, $C_{1-5}$alkyl, $C_{1-5}$alkenyl, $C_{1-5}$alkenylcarbonyl, $C_{2-5}$alkynyl, $C_{2-5}$alkynylcarbonyl and $(CH_2)_m$—C(O)— where m is 2–5;
Z is selected from the group consisting of hydroxy, $C_{1-5}$ alkoxy, phenoxy, phenyl$C_{1-5}$alkoxy, amino, $C_{1-5}$alkylamino, di$C_{1-5}$alkylamino, phenylamino, phenyl$C_{1-5}$alkylamino, piperidin-1-yl substituted piperidin-1-yl (where the substituents are selected from the group consisting of $C_{1-5}$alkyl, $C_{1-5}$alkoxy, halo, aminocarbonyl, $C_{1-5}$alkoxycarbonyl, and oxo;
substituted phenyl$C_{1-5}$alkylamino (where the aromatic substitutents are selected from the group consisting of $C_{1-5}$alkyl, $C_{1-5}$alkoxy, phenyl$C_{1-5}$alkenyloxy, hydroxy, haloen, trifluoromethyl, nitro, nitrite, and amino),
substituted phenoxy (where the aromatic substitutents are selected from the group consisting of $C_{1-5}$alkyl, $C_{1-5}$alkoxy, hydroxy, halogen, trifluorornethyl, nitro, nitrile, and amino),
substituted phenyl$C_{1-5}$alkoxy (where the aromatic substitutents are selected from the group consisting of $C_{1-5}$alkyl, $C_{1-5}$alkoxy, hydroxy, halogen, trifluoromethyl, nitro, nitrile, and amino),
—$OCH_2CH_2(OCH_2CH_2)_sOCH_2CH_2O$—,
—$NHCH_2CH_2(OCH_2CH_2)_sOCH_2CH_2NH$—,
—$NH(CH_2)_pO(CH_2)_qO(CH_2)_pNH$—, —$NH(CH_2)_qNCH_3(CH_2)_sNH$—, —$NH(CH_2)_sNH$—, and $(NH(CH_2)_s)_3N$,
where s, p, and q are independently selected from 1–7 or a pharmaceutically acceptable salt thereof.

2. The method of claim 1 wherein the compound is selected from a group consisting compound 1 and compound 2, having the structures

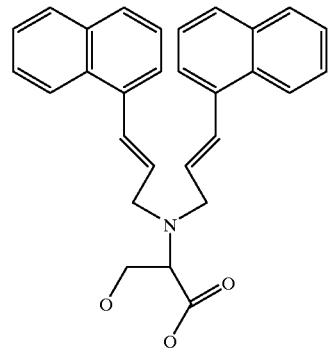

compound 1

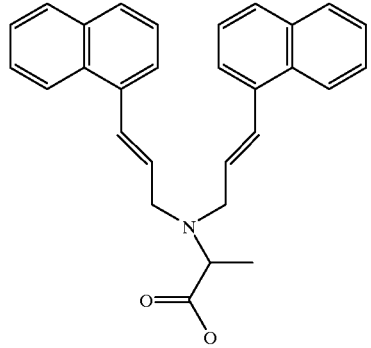

compound 2 and pharmaceutically acceptable salts thereof.

3. A method for treating a disease or condition in which inhibition of neutral sphingomylenase is indicated comprising administering to the individual in need thereof an effective amount of the compound of Formula 1:

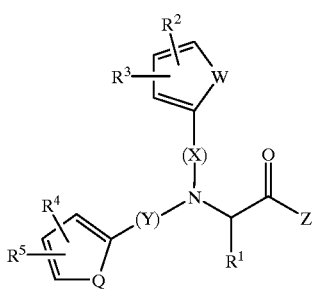

wherein;

R[1] is the side chain of an amino acid, wherein said amino acid is selected from the group consisting of natural α-amino acids of L configuration, natural α-amino acids of D-configuration, α-aminoadipic acid, 4-aminobutanoic acid, 6-aminohexanoic acid, α-aminosubenic acid, 5-arninopentanoic acid, p-aminophenylalanine, α-aminopimetic acid, γ-carboxyglutamic acid, p-carboxyphenylalanine, carnitine, citrulline, α,β-diaminopropionic acid, α,γ-diaminobutyric acid, homocitrulline, homoserine, and statine, where if said side chain contains a protectable group, that group may be protected with a member of the group consisting of succinyl, glutaryl, 3,3-dimethylgiutaryl, $C_{1-5}$alkyl, $C_{1-5}$alkoxycarbonyl, acetyl, N-(9-fluorenylmethoxycarbonyl), trifluoroacetyl, omega-carboxy$C_{1-5}$alkytcarbonyl, t-butoxycarbonyl, benzyl, benzyloxycarbonyl, 2-chlorobenzyloxycarbonyl, phenylsulfonyl, ureido, t-butyl, cinnamoyl, trityl, 4-methyltrityl, 1-(4,4-dimethyl-2,6-dioxocyclohexylidene)ethyl, tosyl, 4-methoxy-2,3,6-trimethylbenzenesulfonyl, phenylureido, and substituted phenylureido (where the phenyl substituents are phenoxy, halo, $C_{1-5}$alkoxycarbonyl);

R[2] and R[3]
are taken together to form a six-membered aromatic ring which is fused to the depicted ring, or,
are independently selected from the group consisting of hydrogen, $C_{1-5}$ alkyl, $C_{1-5}$ alkoxy, hydroxy, halo, trifluoromnethyl, nitro, amino, phenyl, phenoxy, phenyl$C_{1-5}$alkyl, phenyl $C_{1-5}$alkoxy,
substituted phenyl (where the substituents are selected from $C_{1-5}$alky), $C_{1-5}$ alkoxy, hydroxy, halo, trifluoromethyl, nitro, nitrile, and amino),
substituted phenoxy (where the substituents are selected from $C_{1-5}$ alkyl, $C_{1-5}$ alkoxy, hydroxy, halo, trifluoromethyl, nitro, nitrile, and amino),
substituted phenyl$C_{1-5}$alkyl (where the substituents are selected from $C_{1-5}$ alkyl, $C_{1-5}$ alkoxy, hydroxy, halo, trifluoromethyl, nitro, nitrile, and amino),
substituted phenyl$C_{1-5}$alkoxy (where the substituents are selected from $C_{1-5}$ alkyl, $C_{1-5}$ alkoxy, hydroxy, halo, trifluoromethyl, nitro, nitrile, and amino), and
substituted amino (where the substituents are selected from one or more members of the group consisting of $C_{1-5}$alkyl, halosubstituted$C_{1-5}$alkyl, $C_{1-5}$alknyl, $C_{1-5}$alkenyl, phenyl, phenyl$C_{1-5}$alkyl, $C_{1-5}$alkylcarbonyl, halo substituted $C_{1-5}$alkylcarbonyl, carboxy$C_{1-5}$alkyl, $C_{1-5}$alkoxy$C_{1-5}$alkyl, cinnamoyl, naphthylcarbonyl, furylcarbonyl, pyridylcarbonyl, $C_{1-5}$alkylsulfonyl, phenylcarbonyl, phenyl$C_{1-5}$alkylcarbonyl, phenylsulfonyl, phenyl$C_{1-5}$alkylsulfonyl substituted phenylcarbonyl, substituted phenyl$C_{1-5}$alkylcarbonyl, substituted phenylsulfonyl, substituted phenyl$C_{1-5}$alkylsulfonyl, substituted phenyl, and substituted phenyl$C_{1-5}$alkyl [where the aromatic phenyl, phenyl$C_{1-5}$alkyl, phenylcarbonyl, phenyl$C_{1-5}$alkylcarbonyl, phenylsulfonyl, and phenyl$C_{1-5}$alkylsulfonyl substitutents are independently selected from one to five members of the group consisting of $C_{1-5}$alkyl, $C_{1-5}$alkoxy, hydroxy, halogen, trifluoromethyl, nitro, nitrile, and amino]):

R[4] and R[5]
are taken together to form a six-membered aromatic ring which is fused to the depicted ring, or,
are independently selected from the group consisting of hydrogen, $C_{1-5}$ alkyl, $C_{1-5}$ alkoxy, hydroxy, halo, trifluoromethyl, nitro, amino, phenyl, phenoxy, phenyl$C_{1-5}$alkyl, phenyl $C_{1-5}$alkoxy,
substituted phenyl (where the substituents are selected from $C_{1-5}$alkyl, $C_{1-5}$ alkoxy, hydroxy, halo, trifluoromethyl, nitro, nitrile, and amino),
substituted phenoxy (where the substituents are selected from $C_{1-5}$ alkyl, $C_{1-5}$ alkoxy, hydroxy, halo, rfluoromethyl, nitro, nitrile, and amino),
substituted phenyl$C_{1-5}$alkyl (where the substituents are selected from $C_{1-5}$ alkyl, $C_{1-5}$ alkoxy, hydroxy, halo, trifluoromethyl, nitro, nitrile, and amino),
substituted phenyl$C_{1-5}$alkoxy (where the substituents are selected from $C_{1-5}$ alkyl, $C_{1-5}$ alkoxy, hydroxy, halo, trifluoromethyl, nitro, nitrile, and amino), and
substituted amino (where the substituents are selected from one or more members of the group consisting of $C_{1-5}$alkyl, halosubstituted$C_{1-5}$alkyl, $C_{1-5}$alknyl, $C_{1-5}$alkenyl, phenyl, phenyl$C_{1-5}$alkyl, $C_{1-5}$alkylcarbonyl, halo substituted $C_{1-5}$alkylcarbonyl, carboxy$C_{1-5}$alkyl, $C_{1-5}$alkoxy$C_{1-5}$alkyl, cinnamoyl, naphthylcarbonyl, furylcarbonyl, pyridylcarbonyl, $C_{1-5}$alkylsulfonyl, phenylcarbonyl, phenyl$C_{1-5}$alkylcarbonyl, phenylsulfonyl, phenyl$C_{1-5}$alkylsulfonyl substituted phenylcarbonyl, substituted phenyl$C_{1-5}$alkylcarbonyl, substituted phenylsulfonyl, substituted phenyl$C_{1-5}$alkylsulfonyl, substituted phenyl, and substituted phenyl$C_{1-5}$alkyl [where the aromatic phenyl, phenyl$C_{1-5}$alkyl, phenylcarbonyl, pheny$C_{1-5}$alkylcarbonyl, phenylsulfonyl, and phenyl$C_{1-5}$alkylsulfonyl substitutents are independently selected from one to five members of the group consisting of $C_{1-5}$alkyl, $C_{1-5}$alkoxy, hydroxy, halogen, trifluoromethyl, nitro, nitrile, and amino]);

W is selected from the group consisting of —CH=CH—,
Q is selected from the group consisting of —CH=CH—,
X is selected from the group consisting of carbonyl, $C_{1-5}$alkyl, $C_{1-5}$alkenyl, $C_{1-5}$alkenylcarbonyl, $C_{2-5}$alkynyl, $C_{2-5}$alkynylcarbonyl and $(CH_2)_m$—C(O)— where m is 2–5,
Y is selected from the group consisting of carbonyl, $C_{1-5}$alkyl, $C_{1-5}$alkenyl, $C_{1-5}$alkenylcarbonyl, $C_{2-5}$alkynyl, $C_{2-5}$alkynylcarbonyl and $(CH_2)_m$—C(O)— where m is 2–5;
Z is selected from the group consisting of hydroxy, $C_{1-5}$ alkoxy, phenoxy, phenyl$C_{1-5}$alkoxy, amino, $C_{1-5}$alkylamino, di$C_{1-5}$alkylamino, phenylamino, phenyl$C_{1-5}$alkylamino, piperidin-1-yl
substituted piperidin-1-yl (where the substituents are selected from the group consisting of $C_{1-5}$alkyl, C$_{1-5}$alkoxy, halo, aminocarbonyl, C$_{1-5}$alkoxycarbonyl, and oxo;
substituted phenylC$_{1-5}$alkylamnino (where the aromatic substitutents are selected from the group consisting of C$_{1-5}$alkyl, C$_{1-5}$alkoxy, phenylC$_{1-5}$alkenyloxy, hydroxy, halogen, trifluoromethyl, nitro, nitrile, and amino),
substituted phenoxy (where the aromatic substitutents are selected from the group consisting of C$_{1-5}$alkyl, C$_{1-5}$alkoxy, hydroxy, halogen, trifluoromethyl, nitro, nitrile, and amino),
substituted phenylC$_{1-5}$alkoxy (where the aromatic substitutents are selected from the group consisting of C$_{1-5}$alkyl, C$_{1-5}$alkoxy, hydroxy, halogen, trifluorornethyl, nitro, nitrile, and amino),
—OCH$_2$CH$_2$(OCH$_2$CH$_2$)$_s$OCH$_2$CH$_2$O—,
—NHCH$_2$CH$_2$(OCH$_2$CH$_2$)$_s$OCH$_2$CH$_2$NH—,
—NH(CH$_2$)$_p$O(CH$_2$)$_q$O(CH$_2$)$_p$NH—, —NH(CH$_2$)$_q$NCH$_3$(CH$_2$)$_s$NH—, —NH(CH$_2$)$_s$NH—, and (NH(CH$_2$)$_s$)$_3$N,
where s, p, and q are independently selected from 1–7 or a pharmaceutically acceptable salt thereof.

4. A neutral sphingomyelinase inhibiting compound of formula II

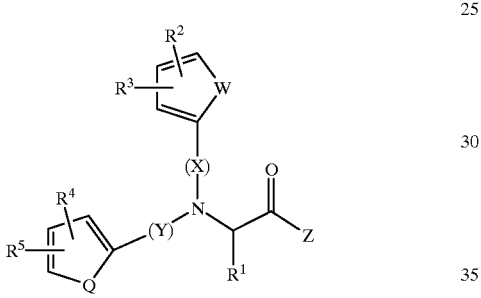

wherein:
R$^1$ is the side chain of an amino acid Cl, where if said side chain contains a protectable group, that group may be protected with a member of the group consisting of succinyl, glutaryl, 3,3-dimethylglutaryl, C$_{1-5}$alkyl, C$_{1-5}$alkoxycarbonyl, acetyl, N-(9-fluorenylmethoxycarbonyl), trifluoroacetyl, omega-carboxyC$_{1-5}$alkylcarbonyl, t-butoxycarbonyl, benzyl, benzyloxycarbonyl, 2-chlorobenzyloxycarbonyl, phenylsulfonyl, ureido, t-butyl, cinnamoyl, trityl, 4-methyltrityl, 1-(4,4-dimethyl-2,6-dioxocyclohexylidene)ethyl, tosyl, 4-methoxy-2,3,6-trimethylbenzenesulfonyl, phenylureido, and substituted phenylureido (where the phenyl substituents are phenoxy, halo, C$_{1-5}$alkoxycarbonyl);

R$^2$ and R$^3$
are taken together to form a six-membered aromatic ring which is fused to the depicted ring, or
are independently selected from the group consisting of hydrogen, C$_{1-5}$ alkyl, C$_{1-5}$ alkoxy, hydroxy, halo, trifluoromethyl, nitro, amino, phenyl, phenoxy, phenylC$_{1-5}$alkyl, phenyl C$_{1-5}$alkoxy,
substituted phenyl (where the substituents are selected from C$_{1-5}$alkyl, C$_{1-5}$ alkoxy, hydroxy, halo, trifluoromethyl, nitro, nitrile, and amino),
substituted phenoxy (where the substituents are selected from C$_{1-5}$alkyl, C$_{1-5}$ alkoxy, hydroxy, halo, trifluoromethyl, nitro, nitrile, and amino),
substituted phenylC$_{1-5}$alkyl (where the substituents are selected from C$_{1-5}$ alkyl, C$_{1-5}$ alkoxy, hydroxy, halo, trifluoromethyl, nitro, nitrile, and amino),
substituted phenylC$_{1-5}$alkoxy (where the substituents are selected from C$_{1-5}$ alkyl, C$_{1-5}$ alkoxy, hydroxy, halo, trifluoromethyl, nitro, nitrile, and amino), and
substituted amino (where the substituents are selected from one or more members of the group consisting of C$_{1-5}$alkyl, halosubstitutedC$_{1-5}$alkyl, C$_{1-5}$alknyl, C$_{1-5}$alkenyl, phenyl, phenylC$_{1-5}$alkyl, C$_{1-5}$alkylcarbonyl, halo substituted C$_{1-5}$alkylcarbonyl, carboxyC$_{1-5}$alkyl, C$_{1-5}$alkoxyC$_{1-5}$alkyl, cinnamoyl, naphthylcar-bonyl, furylcarbonyl, pyridylcarbonyl, C$_{1-5}$alkylsulfonyl, phenylcarbonyl, phenylC$_{1-5}$alkylcarbonyl, phenylsulfonyl, phenylC$_{1-5}$alkylsulfonyl substituted phenylcarbonyl, substituted phenylC$_{1-5}$alkylcarbonyl, substituted phenylsulfonyl, substituted phenylC$_{1-5}$alkylsulfonyl, substituted phenyl, and substituted phenylC$_{1-5}$alkyl [where the aromatic phenyl, phenylC$_{1-5}$alkyl, phenylcarbonyl, phenylC$_{1-5}$alkylcarbonyl, phenylsulfonyl, and phenylC$_{1-5}$alkylsulfonyl substitutents are independently selected from one to five members of the group consisting of C$_{1-5}$alkyl, C$_{1-5}$alkoxy, hydroxy, halogen, trifluoromethyl, nitro, nitrile, and amino]);

R$^4$ and R$^5$
are taken together to form a six-membered aromatic ring which is fused to the depicted ring, or
are independently selected from the group consisting of hydrogen, C$_{1-5}$ alkyl, C$_{1-5}$ alkoxy, hydroxy, halo, trifluoromethyl, nitro, amino, phenyl, phenoxy, phenylC$_{1-5}$alkyl, phenyl C$_{1-5}$alkoxy,
substituted phenyl (where the substituents are selected from C$_{1-5}$alkyl, C$_{1-5}$ alkoxy, hydroxy, halo, trifluoromethyl, nitro, nitrile, and amino),
substituted phenoxy (where the substituents are selected from C$_{1-5}$ alkyl, C$_{1-5}$ alkoxy, hydroxy, halo, trifluoromethyl, nitro, nitrile, and amino),
substituted phenylC$_{1-5}$alkyl (where the substituents are selected from C$_{1-5}$ alkyl, C$_{1-5}$ alkoxy, hydroxy, halo, trifluoromethyl, nitro, nitrile, and amino),
substituted phenylC$_{1-5}$alkoxy (where the substituents are selected from C$_{1-5}$ alkyl, C$_{1-5}$ alkoxy, hydroxy, halo, trifluoromethyl, nitro, nitrile, and amino), and
substituted amino (where the substituents are selected from one or more members of the group consisting of C$_{1-5}$alkyl, halosubstitutedC$_{1-5}$alkyl, C$_{1-5}$alknyl, C$_{1-5}$alkenyl, phenyl, phenylC$_{1-5}$alkyl, C$_{1-5}$alkylcarbonyl, halo substituted C$_{1-5}$alkylcarbonyl, carboxyC$_{1-5}$alkyl, C$_{1-5}$alkoxyC$_{1-5}$alkyl, cinnamoyl, naphthylcarbonyl, furylcarbonyl, pyridylcarbonyl, C$_{1-5}$alkylsulfonyl, phenylcarbonyl, phenylC$_{1-5}$alkylcarbonyl, phenylsulfonyl, phenylC$_{1-5}$alkylsulfonyl substituted phenylcarbonyl, substituted phenylC$_{1-5}$alkylcarbonyl, substituted phenylsulfonyl, substituted phenylC$_{1-5}$alkylsulfonyl, substituted phenyl, and substituted phenylC$_{1-5}$alkyl [where the aromatic phenyl, phenylC$_{1-5}$alkyl, phenylcarbonyl, phenylC$_{1-5}$alkylcarbonyl, phenylsulfonyl, and phenylC$_{1-5}$alkylsulfonyl substitutents are independently selected from one to five members of the group consisting of C$_{1-5}$alkyl, C$_{1-5}$alkoxy, hydroxy, halogen, trifluoromethyl, nitro, nitrile, and amino]);

W is selected from the group consisting of —CH═CH—;
Q is selected from the group consisting of —CH═CH—;
X is selected from the group consisting of C$_{2-5}$alkynyl, and C$_{2-5}$alkynylcarbony;
Y is selected from the group consisting of C$_{2-5}$alkynyl, and C$_{2-5}$alkynylcarbonyl;

Z is selected from the group consisting of hydroxy, $C_{1-5}$alkoxy, phenoxy, phenyl$C_{1-5}$alkoxy, amino, $C_{1-5}$alkylamino, di$C_{1-5}$alkylamino, phenylamino, phenyl$C_{1-5}$alkylamino, piperidin-1-yl substituted piperidin-1-yl (where the substituents are selected from the group consisting of $C_{1-5}$alkyl, $C_{1-5}$alkoxy, halo, aminocarbonyl, $C_{1-5}$alkoxycarbonyl, and oxo;

substituted phenyl$C_{1-5}$alkylamino (where the aromatic substitutents are selected from the group consisting of $C_{1-5}$alkyl, $C_{1-5}$alkoxy, phenyl$C_{1-5}$alkenyloxy, hydroxy, halogen, trifluoromethyl, nitro, nitrile, and amino), substituted phenoxy (where the aromatic substitutents are selected from the group consisting of $C_{1-5}$alkyl, $C_{1-5}$alkoxy, hydroxy, halogen, trifluoromethyl, nitro, nitrile, and amino), substituted phenyl$C_{1-5}$alkoxy (where the aromatic substitutents are selected from the group consisting of $C_{1-5}$alkyl, $C_{1-5}$alkoxy, hydroxy, halogen, trifluoromethyl, nitro, nitrile, and amino), —$OCH_2CH_2(OCH_2CH_2)_sOCH_2CH_2O$—, —$NHCH_2CH_2(OCH_2CH_2)_sOCH_2CH_2NH$—, —$NH(CH_2)_pO(CH_2)_qO(CH_2)_pNH$, —$NH(CH_2)_qNCH_3(CH_2)_sNH$—, —$NH(CH_2)_sNH$—, and $(NH(CH_2)_s)_3N$, where s, p, and q are independently selected from 1–7 or a pharmaceutically acceptable salt thereof.

5. The compound of claim 4 wherein $R^1$ is the side chain of an amino acid Cl, where if said side chain contains a protectable group, that group may be protected with a member of the group consisting of succinyl, glutaryl, 3,3-dimethylglutaryl, $C_{1-5}$alkyl, $C_{1-5}$alkoxycarbonyl, acetyl, N-(9-fluorenylmethoxycarbonyl), trifluoroacetyl, omega-carboxy$C_{1-5}$alkylcarbonyl, 1-butoxycarbonyl, benzyl, benzyloxycarbonyl, 2-chlorobenzyloxycarbonyl, phenylsulfonyl, ureido, t-butyl, cinnamoyl, trityl, 4-methyltrityl, 1-(4,4-dimethyl-2,6-dioxocyclohexylidene)ethyl, tosyl, 4-methoxy-2,3,6-trimethylbenzenesulfonyl, phenylureido, and substituted phenylureido (where the phenyl substituents are phenoxy, halo, $C_{1-5}$alkoxycarbonyl);

$R^2$ and $R^3$ are joined into one six member ring, or are both methoxy;

$R^4$ and $R^5$ are joined into one six member ring, or are both methoxy;

W is selected from the group consisting of —CH=CH—;

Q is selected from the group consisting of —CH=CH—;

X is $C_{2-5}$alkynyl;

Y is $C_{2-5}$alkynyl;

Z is selected from the group consisting of hydroxy, $C_{1-5}$alkoxy, phenoxy, phenyl$C_{1-5}$alkoxy, amino, $C_{1-5}$alkylamino, di$C_{1-5}$alkylamino, phenylamino, phenyl$C_{1-5}$alkylamino, piperidin-1-yl substituted piperidin-1-yl (where the substituents are selected from the group consisting of $C_{1-5}$alkyl, $C_{1-5}$alkoxy, halo, aminocarbonyl, $C_{1-5}$alkoxycarbonyl, and oxo;

substituted phenyl$C_{1-5}$alkylamino (where the aromatic substitutents are selected from the group consisting of $C_{1-5}$alkyl, $C_{1-5}$alkoxy, phenyl$C_{1-5}$alkenyloxy, hydroxy, halogen, trifluoromethyl, nitro, nitrile, and amino), substituted phenoxy (where the aromatic substitutents are selected from the group consisting of $C_{1-5}$alkyl, $C_{1-5}$alkoxy, hydroxy, halogen, trifluoromethyl, nitro, nitrile, and amino), substituted phenyl$C_{1-5}$alkoxy (where the aromatic substitutents are selected from the group consisting of $C_{1-5}$alkyl, $C_{1-5}$alkoxy, hydroxy, halogen, trifluoromethyl, nitro, nitrile, and amino), —$OCH_2CH_2(OCH_2CH_2)_sOCH_2CH_2O$—, —$NHCH_2CH_2(OCH_2CH_2)_sOCH_2CH_2NH$—, —$NH(CH_2)_pO(CH_2)_qO(CH_2)_pNH$—, —$NH(CH_2)_qNCH_3(CH_2)_sNH$—, —$NH(CH_2)_sNH$—, and $(NH(CH_2)_s)_3N$, where s, p, and q are independently selected from 1–7 or a pharmaceutically acceptable salt thereof.

6. A compound of the formula

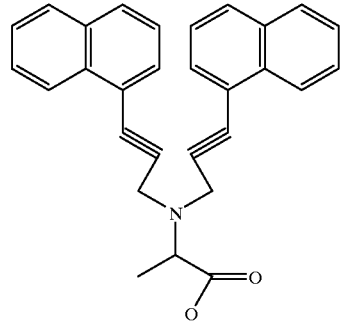

compound 17 or a pharmaceutically acceptable salt thereof.

7. A pharmaceutical composition comprising the compound of claim 4 and a pharmaceutically acceptable carrier.

8. A method for treating a patient suffering from a disease or condition in which inhibition of neutral sphingomyelinase is indicated comprising administering to the individual in need thereof an effective amount of a compound of formula II of claim 4.

* * * * *